(12) United States Patent
Jensen

(10) Patent No.: US 12,138,238 B2
(45) Date of Patent: Nov. 12, 2024

(54) COMPOSITIONS COMPRISING N-ACETYL METHYL GABA AND RELATED METHODS

(71) Applicant: MBI Distributing, Lindon, UT (US)

(72) Inventor: Ned L. Jensen, Alpine, UT (US)

(73) Assignee: MBI Distributing, Lindon, UT (US)

( * ) Notice: Subject to any disclaimer, the term of this patent is extended or adjusted under 35 U.S.C. 154(b) by 0 days.

(21) Appl. No.: 18/359,271

(22) Filed: Jul. 26, 2023

(65) Prior Publication Data

US 2023/0364048 A1 Nov. 16, 2023

Related U.S. Application Data

(62) Division of application No. 17/245,861, filed on Apr. 30, 2021, now Pat. No. 11,957,653.

(60) Provisional application No. 63/018,185, filed on Apr. 30, 2020.

(51) Int. Cl.
| | |
|---|---|
| A61K 31/22 | (2006.01) |
| A61K 9/127 | (2006.01) |
| A61K 31/4045 | (2006.01) |
| A61K 47/10 | (2017.01) |
| A61K 47/14 | (2017.01) |
| A61K 47/24 | (2006.01) |
| A61P 15/00 | (2006.01) |
| A61P 25/06 | (2006.01) |
| A61P 25/20 | (2006.01) |
| A61P 25/22 | (2006.01) |
| A61P 25/28 | (2006.01) |
| C07C 231/14 | (2006.01) |

(52) U.S. Cl.
CPC ............. *A61K 31/22* (2013.01); *A61K 9/127* (2013.01); *A61K 31/4045* (2013.01); *A61K 47/10* (2013.01); *A61K 47/14* (2013.01); *A61K 47/24* (2013.01); *A61P 15/00* (2018.01); *A61P 25/06* (2018.01); *A61P 25/20* (2018.01); *A61P 25/22* (2018.01); *A61P 25/28* (2018.01); *C07C 231/14* (2013.01)

(58) Field of Classification Search
None
See application file for complete search history.

(56) References Cited

U.S. PATENT DOCUMENTS

| | | | |
|---|---|---|---|
| 4,372,953 A | 2/1983 | Uchida et al. | |
| 2006/0251597 A1 | 11/2006 | Yu et al. | |
| 2008/0044499 A1 | 2/2008 | Ozeki et al. | |
| 2013/0210758 A1 | 8/2013 | Keller | |
| 2015/0087679 A1 | 3/2015 | Helmi et al. | |
| 2020/0138783 A1* | 5/2020 | Rinaldi | A61K 9/0056 |

FOREIGN PATENT DOCUMENTS

| | | |
|---|---|---|
| CN | 101575311 B | 5/2011 |
| JP | 57-158767 A | 9/1982 |

OTHER PUBLICATIONS

"Chemical Abstracts Service No. 32039-11-5 Butanoic acid, 4-(acetylamino)-, methyl ester"; Sagechem; www.sagechem.com/product/989592; accessed Jan. 30, 2020.
"Chemical Abstracts Service No. 914306-27-7(Butanoic acid, 4-(acetylamino)-, propyl ester) Product Description"; Chemical Book; https://www.chemicalbook.com/ChemicalProductProperty_US_CB91865937.aspx; 1 page, accessed Jan. 30, 2020.
Aberhart, DJ et al. "Stereochemistry of Lysine 2,3-Aminomutase," Journal of the American Chemical Society (1981), 103 (22): pp. 6750-6752.
Basu, K. et al., "Efficient acetylation of primary amines and amino acids in environmentally benign brine solution using acetyl chloride" J. Chemical Sci. (2013) 125(3): pp. 607-613.
Carter, H.E. et al., "Azlactones:III.Acylation of Amino Acids in Pyridine" J. Biol. Chem.(1941) 138: pp. 619-626.
Darsi, S.S. et al., "Studies on N-acetylation of Anilines with Acetyl Chloride using Phase Transfer Catalysts in Different Solvents" Der Pharma Chemica (2011) 3(5):35-38.
International Searching Authority of the US Patent and Trademark Office, "International Search Report and Written Opinion" issued Sep. 16, 2021 in PCT Appln. No. PCT/US21/30213 (8 pages).
Johnson, DE et al., "Gas-Liquid Chromatography of Amino Acid Derivatives," Analytical Chemistry (1961), 33 (6): pp. 669-673.
Kricheldorf, HR "Nitrogen-15 NMR Spectroscopy. 30—Structure/Shift Relationships of Oligopeptides and Copolypeptides, Including Gramicidin S," Organic Magnetic Resonance (1981), 15 (2): pp. 162-177.
Kubyshkin, V. et al., "Energetic contribution to both acidity and conformational stability in peptide models," New J. Chem., 2016, 40, pp. 5209-5220.
Liu, Q et al., "Opposing Effects of Side-Chain Flexibility and Hydrogen Bonding on the Thermal, Mechanical, and Rheological Properties of Supramolecularly Cross-Linked Polyesters," Macromolecules (2018), 51 (22): pp. 9294-9305.
Nikishin, GI et al., "Free-radical addition of N-alkylacetamides to methyl acrylate," Doklady Chemistry (1963), vol. 152, No. 4: pp. 879-881.
Papadopoulos, GN et al., "One-Pot Amide Bond Formation from Aldehydes and Amines via a Photoorganocatalytic Activation of Aldehydes," Journal of Organic Chemistry (2016), 81 (16): pp. 7023-7028.
Phukan, K. et al., "Mild and Useful Method for N-Acylation of Amines" Synthet. Comms. (2009) 39(15):pp. 2694-2701.

(Continued)

*Primary Examiner* — Celeste A Roney
(74) *Attorney, Agent, or Firm* — Amin Wasserman Gurnani LLP; Valerie Neymeyer-Tynkov; George M. Carrera, Jr.

(57) ABSTRACT

The present invention is directed to compositions comprising N-Acetyl Methyl GABA, methods of preparing N-Acetyl Methyl GABA and compositions including N-Acetyl Methyl GABA, and methods of using N-Acetyl Methyl GABA for instance to improve sleep and control anxiety.

18 Claims, 4 Drawing Sheets

(56) References Cited

OTHER PUBLICATIONS

Reimlinger, H., et al. "Additions of pyrazole to activated multiple bonds, I," Chemische Berichte (1964), 97 (2): pp. 331-338.
Tsuge, O. et al., "Synthetic Versatility of N(Silylmethyl)imines: Water-Induced Generation of N-Protonated Azomethine Ylides of Nonstabilized Type and Fluoride-Induced Generation of 2-Azallyl Anions," Bulletin of the Chemical Society of Japan (1986), 59: pp. 2537-2545.
Veith, HJ et al. "Mass spectrometric behavior of nitrogen compounds. 15. New mass spectrometric fragmentation reactions of ,-disubstituted alkanes," Helvetica Chimica Acta (1971), 54 (2): pp. 653-680.

* cited by examiner

COMPOSITIONS COMPRISING N-ACETYL METHYL GABA AND RELATED METHODS

CROSS-REFERENCE TO RELATED APPLICATIONS

This application claims the benefit of U.S. patent application Ser. No. 17/245,861, filed Apr. 30, 2021, which claims the benefit of US Provisional Patent Application No. 63/018,185, filed Apr. 30, 2020. Each of these applications is incorporated by reference herein in its entirety.

FIELD OF THE INVENTION

The present invention relates to compositions comprising N-Acetyl Methyl GABA, methods of preparing N-Acetyl Methyl GABA and preparing compositions including N-Acetyl Methyl GABA, and methods of using N-Acetyl Methyl GABA for instance to improve sleep and reduce anxiety and stress.

BACKGROUND

GABA (gamma-aminobutyric acid; $NH_2CH_2CH_2CH_2C(O)OH$) acts as a neurotransmitter in the brain, controlling anxiety and contributing to motor control and many other functions of the cortex. GABA is problematic as an oral drug because the polar ends (amino-($-NH_2$); carboxyl-($-COOH$)) of the GABA molecule hinder its transport across the blood-brain barrier. GABA receptor agonists may provide anxiolytic and stress-relieving effects, and may for instance reduce muscle spasms.

Due to stress and lifestyle, many people find it difficult to fall or stay asleep, or to feel calm. Falling asleep is a major problem in the modern world.

The use of GABA as for instance a sleep aid is limited by its relative inability to pass the blood-brain barrier. Phenylated GABA derivatives such as fenibut are used as a sleep aid, however, fenibut has been banned in some jurisdictions. Possibly, its phenol metabolites cause neurotoxicity in the brain. Kavinace® was a sleep aid that included a phenylated GABA (4-amino-3-phenylbutyric acid). However, that version of the sleep aid has been discontinued.

SUMMARY OF THE INVENTION

The present invention is directed to N-Acetyl Methyl GABA and compositions thereof. The present invention is also directed to a process for preparing N-Acetyl Methyl GABA, comprising, consisting essentially of, or consisting of the steps of: methylating the carboxyl group of GABA and acetylating the amino group of GABA to prepare N-Acetyl Methyl GABA; and optionally, purifying the N-Acetyl Methyl GABA. In addition, the present invention is directed to methods for aiding sleep, treating insomnia, and reducing anxiety and/or reducing stress in a subject, and related methods.

In an embodiment, a composition of this invention comprises N-Acetyl Methyl GABA. In an embodiment, a composition of this invention comprises, consists essentially of, or consists of, N-Acetyl Methyl GABA made by a process of this invention.

In an embodiment, this invention comprises a process for preparing N-Acetyl Methyl GABA, comprising the steps of:
a. methylating the carboxyl group of GABA;
b. acetylating the amino group of GABA to prepare N-Acetyl Methyl GABA; and then
c. optionally purifying the N-Acetyl Methyl GABA.

In an embodiment, this invention comprises methods of aiding sleep and/or treating insomnia, reducing stress and/or anxiety, and improving qualities and symptoms identified in the Examples and throughout this application.

DETAILED DESCRIPTION

Figure 1:
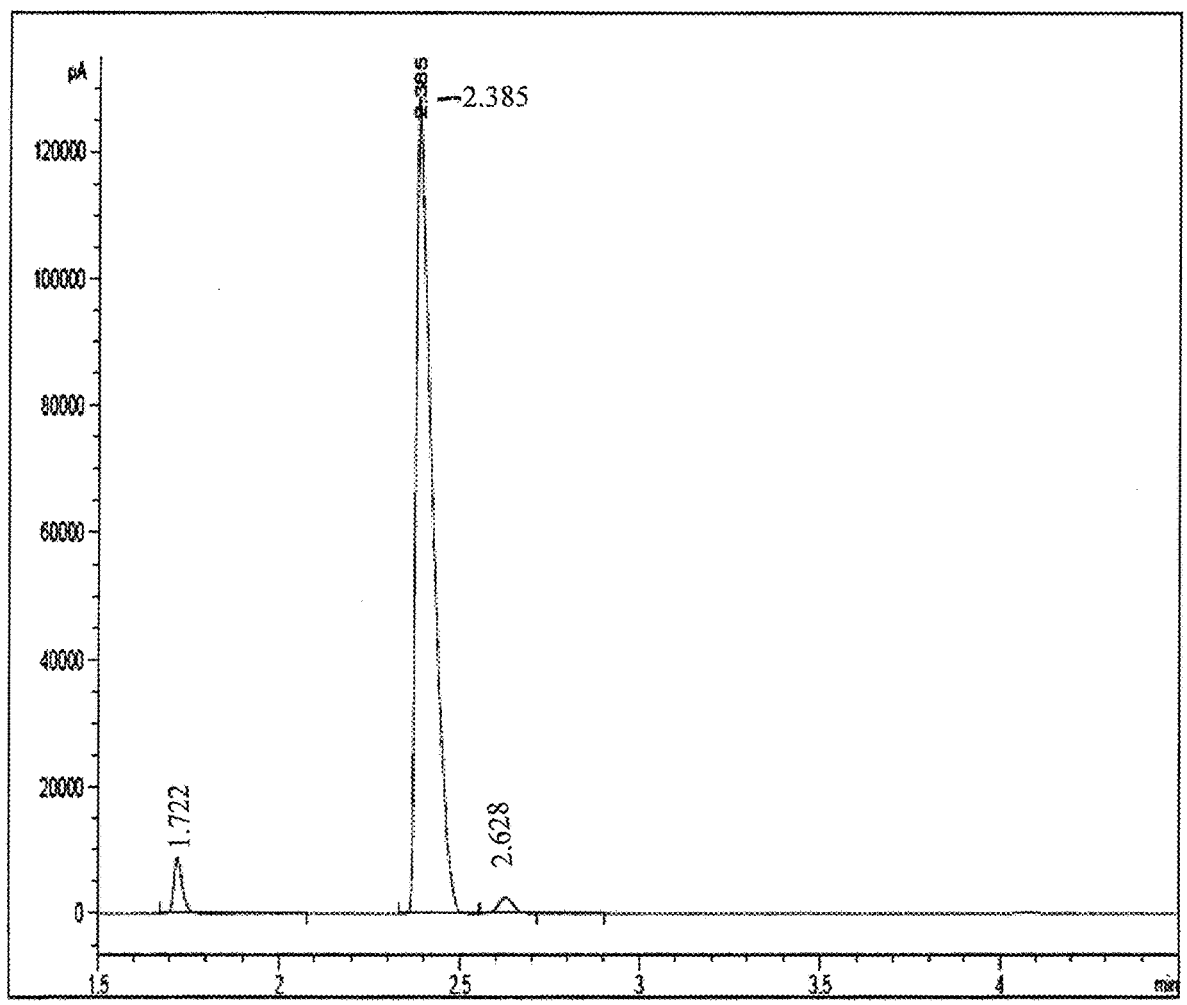
FIG. 1 represents a gas chromatogram of an N-Acetyl Methyl GABA distillate of this invention.

The present invention is directed to N-Acetyl Methyl GABA and compositions comprising, consisting essentially of, or consisting of N-Acetyl Methyl GABA. N-Acetyl Methyl GABA has the chemical structure $CH_3C(O)NHCH_2CH_2CH_2C(O)OCH_3$ (Molecular Formula: $C_7H_{13}O_3N$. Molecular Weight: 159.183). The present invention is also directed to methods for preparing N-Acetyl Methyl GABA, and methods for administering N-Acetyl Methyl GABA and its composition to a subject.

In the brain and overall central nervous system, GABA may block GABA receptors and reduce anxiety and stress, allowing a subject to feel more relaxed and enjoy improved sleep, mood, mental clarity and memory, daytime energy, and other beneficial effects. In addition, by reducing anxiety and stress, GABA can decrease body aches and pains, stress headaches, and digestive issues.

According to the present invention, without being bound by theory, N-Acetyl Methyl GABA administered to a human or other mammal is transported across the blood-brain barrier, where it may be converted into GABA, and reduce anxiety and stress in a subject. Also without being bound by theory, metabolites of N-Acetyl Methyl GABA include an acetate group and a methyl group, which may be used in other biochemical reactions in the brain and/or provide effects in the brain. In an embodiment, after using N-Acetyl Methyl GABA as an overnight sleep aid, human subjects experience uninterrupted sleep and little to no grogginess upon waking at the end of the sleep period, in contrast to grogginess upon waking for instance as is common with other sleep aids. In an embodiment, general body inflammation and aches and pains in the subject are also reduced. In an embodiment, the subject's mind is clear and attitude is positive after sleep aided by N-Acetyl Methyl GABA.

Without being bound by theory, these effects are or may be due to N-Acetyl Methyl GABA action as an anxiolytic agent.

The present invention is directed in part to a novel synthesis method for preparing N-Acetyl Methyl GABA comprising, consisting essentially of, or consisting of the steps of methylating the carboxyl end of the GABA molecule and then acetylating the amino end to prepare N-Acetyl Methyl GABA, and then optionally, purifying the N-Acetyl Methyl GABA. Without being bound by theory, these modifications render GABA non-polar and able to be transported across the blood-brain barrier.

In an embodiment, the present method uses only two synthesis steps and safe recoverable solvents, yields about 95% (highly pure) product (N-Acetyl Methyl GABA), and optionally includes a third (purification) step to increase purity of the N-Acetyl Methyl GABA. Reaction conditions are safe and easily controlled. In an embodiment, during said acetylation step, a neutral or basic pH (for instance about pH 6-8.5, or pH 6.5-8) is maintained, and a solvent with a lower boiling point than N-Acetyl Methyl GABA is used. Other synthesis steps may provide low yields of N-Acetyl Methyl GABA and/or use undesirable or dangerous solvents, and may for instance require an extraction procedure which decreases yield and uses more solvent(s) than the present method. Solvent extraction would require two more steps and is messy and time-consuming, requiring drying of the product as well. Due to solvent volatility and the low boiling point of the product, much of the product could be lost in the drying step. Other synthesis steps also include reaction conditions that may be violent and unsafe to personnel and/or the environment, such as the reaction of acetyl chloride with substrate. Some solvents described in the art are carcinogenic and toxic to the body, such as DMF (dimethylformamide), methylene chloride, acetonitrile, pyridine, and are not preferred in the present invention.

In an embodiment, before the optional purifying step, N-Acetyl Methyl GABA prepared according to this invention is at least 85% pure, preferably at least 90% pure, more preferably at least 95% pure; and/or after said purifying step, said N-Acetyl Methyl GABA is at least 90%, at least 91%, at least 92%, at least 93%, at least 94%, at least 95%, at least 96%, at least 97%, at least 98%, at least 99%, or about 100% pure. In an embodiment, the N-Acetyl Methyl GABA is 98% to 100% pure. In an embodiment, a composition of the present invention consists essentially of N-Acetyl Methyl GABA having the purity levels described above, and for instance as described in FIG. 1.

In an embodiment, before the optional purifying step, the synthesis of N-Acetyl Methyl GABA according to this invention includes a high yield of about 80-100% w/w according to theoretical weight; in an embodiment, a high yield of about 85-100% w/w, a high yield of about 90-100% w/w, a high yield of about 95-100% w/w, a high yield of about 98-100% w/w, and/or a high yield of about 100% based on theoretical weight.

The below definitions and discussion are intended to guide understanding but are not intended to be limiting with regard to other disclosures in this application. Throughout this application, references to percentage (%) of compositions of the present invention refers to the % by weight of a given substance to the total weight of the composition being discussed, also signified by "w/w" or "wt/wt", unless stated otherwise.

A "composition" according to the present invention comprises, consists essentially of, or consists of, N-Acetyl Methyl GABA. A composition of this invention may be pure N-Acetyl Methyl GABA, for instance at least 85%-100% including for instance at least 90%, 95%, 98%, 99%, or about 100% pure. A composition of the present invention may be a nutraceutical or pharmaceutical composition, formulated into nutraceutical or pharmaceutical dosage forms comprising for instance liquids, emulsions, tablets, capsules, powders, chews, gummies, transdermals, injectables, suppositories, dietary supplements, topical creams or gels, lozenges, pills, and so forth. In an embodiment, a composition of the present invention is in solid, liquid, or semi-liquid form, for instance as prepared in Example 1 Step 2, comprising at least 95% w/w N-Acetyl Methyl GABA. In an embodiment, a composition of this invention is for oral administration to a subject, with pharmaceutically and/or nutraceutically acceptable ingredients such as discussed below. In an embodiment, N-Acetyl Methyl GABA is the active ingredient of the composition.

In an embodiment, without being bound by theory, a composition comprising N-Acetyl Methyl GABA according to this invention is administered with an effective amount of N-Acetyl Methyl GABA to a subject, so that the N-Acetyl Methyl GABA reaches the subject's bloodstream and tissues including brain tissue, for instance to aid sleep by improving or achieving a good to excellent period of sleep, and/or to reduce anxiety or to treat insomnia or to otherwise act on and help the subject as described herein. In an embodiment, N-Acetyl Methyl GABA and/or its metabolites or other components reaches the subject's bloodstream and tissues including brain tissues and other CNS tissue to act at GABA receptors to for instance reduce anxiety and/or stress in the subject. In an embodiment, an "effective amount" of N-Acetyl Methyl GABA to be administered to a human subject is about 10 mg to about 1000 mg (preferably orally administered, preferably an adult human subject). In an embodiment, this amount may be higher or lower than the above range, for instance 1 mg to 2000 mg, for instance 200-600 mg or e.g. 300 mg as discussed throughout this application. A daily dose according to this invention may be limited by safety regulations for instance as promulgated by a regulatory agency. In an embodiment, N-Acetyl Methyl GABA is present in an amount of about 1% to about 100% (w/w) of a composition of this invention. In an embodiment, N-Acetyl Methyl GABA is present in an amount of about 0.1-100% (w/w), 1-50% (w/w), 1-30% (w/w), 2-20% (w/w) of a composition of this invention. In an embodiment, N-Acetyl Methyl GABA is present in an amount of about 10-20% (w/w), 14-16% (w/w), or about 15% (w/w) of a composition of this invention. In an embodiment, N-Acetyl Methyl GABA is present in an amount of about 3-5% w/w of a composition of this invention. For instance, as shown in Examples 3-6, a composition of this invention may include about 300 mg N-Acetyl Methyl GABA in a serving size of about 8 g (2 liquid teaspoons) of a composition of this invention, for instance to improve mood, energy levels, sleep quality, and other parameters discussed in the Examples. In an embodiment, the composition is about 3-4% N-Acetyl Methyl GABA (w/w) (0.3 g/8 g*100%). Without being bound by theory, the N-Acetyl Methyl GABA may be metabolized to GABA in the subject's body, preferably once past the subject's blood-brain barrier. In a non-human mammal, a dose may be about the same as in a human, adjusted per kilogram of weight of the mammal. In an embodiment, an "effective amount" of N-Acetyl Methyl GABA to be administered to a subject, for instance to aid sleep or to reduce anxiety in a human adult subject, is a daily dose of about 200-600 mg. In an embodiment, a "daily dose" of N-Acetyl Methyl GABA to be administered to an adult human subject in a method of this invention is about 200-600 mg, such as 200 mg or 300 mg or 400 mg or other amounts within said range such as 250 mg-400 mg N-Acetyl Methyl GABA.

In an embodiment, a composition of the present invention is in the form described in Example 1 Step 2 or Step 3 of this application. A composition of the present invention may further comprise one or more active ingredients to enhance sleep and/or relaxation, as well as excipients, additives, and/or other substances. In an embodiment, a composition of this invention is in the form of an emulsion of a liposome. In an embodiment, the liposome comprises liquid lecithin, sodium lauroyl lactylate and/or sodium stearoyl lactylate, butylene glycol and glycerine. Without being bound by theory, liposomes enhance the absorption of N-Acetyl Methyl GABA into the bloodstream and/or the brain. In an embodiment, melatonin is added to the composition to enhance the effects of the composition in an embodiment in a synergistic manner. In an embodiment, melatonin may be added to a composition of this invention; in an embodiment, melatonin is added in amount of about 1-10 mg, for instance 5 mg, for instance as a daily dose to an adult human with a daily dose of N-Acetyl Methyl GABA. See for instance Examples 3-6 for further examples of a composition of this invention. In an embodiment, a composition of this invention includes an oil such as MCT (medium-chain triglyceride) oil, vegetable oil, coconut oil, palm oil palm kernel oil, sesame oil, soybean oil, almond oil, rapeseed oil, sunflower oil, corn oil, peanut oil, olive oil, castor oil, safflower oil, and the like. An oil may be fractionated, for instance removing long chain fatty acids from the oil resulting in medium chain triglycerides (e.g. MCT oil). In an embodiment, a composition of this invention includes flavors including natural flavors such as orange, bitter masking agent (e.g. a maple derivative), cinnamon, and/or peppermint, and sweeteners/stabilizers such as xylitol, mannitol, dextrose, glucose, sucrose, fructose, sorbitol, and the like, and/or natural sweeteners such as stevia, luo han guo, and/or glycerine. In an embodiment, a composition of this invention includes preservatives such as glycerine, potassium sorbate, and/or vitamin E. In an embodiment, a natural coloring agent is included in a composition of this invention, such as curcumin. In an embodiment, a thickener and stabilizer such as guar gum may be added to a composition of this invention. In an embodiment, an ingredient added to a composition of this invention may serve more than one function, or may serve only 1 specified function.

In an embodiment, a composition of this invention comprises (w/w) about 3-5% N-Acetyl Methyl GABA; 55-75% water; 10-20% preservatives such as glycerine, potassium sorbate and/or vitamin E oil; 4-8% oil such as MCT oil; 5-10% lecithin or suitable substitute; 2-10% flavoring and/or sweetening agent such as orange flavor, xylitol, stevia extract (e.g. 90%), bitter mask powder, luo han guo (e.g. 50%), peppermint oil, and/or cinnamon; 0.1-3% thickener/stabilizer including for instance guar gum; and optionally 0.1-10% w/w additional agents such as melatonin (typically about 0.05-0.1% w/w).

In an embodiment, combining a suitable solvent combination such as water, glycerine, butylene glycol with the liquid lecithin and a suitable surfactant such as sodium lauroyl lactylate, sodium stearoyl lactylate or Tween 60 makes the lecithin form hollow spheres which encloses the active ingredients: N-Acetyl Methyl GABA and optionally Melatonin. Without being bound by theory, these spheres form by lining up the phosphorus moiety of the lecithin on the outside of the sphere and the lipid end on the inside of the sphere. These spheres are carried into the body and blood stream where they combine with cell membranes to release the active ingredients inside the cell. In an embodiment, liposomes, liposome emulsions, and other delivery methods for N-Acetyl Methyl GABA are prepared according to methods known in the art.

In an embodiment, a composition of this invention is in the form of a capsule for instance composed of gelatin or cellulose such as a softgel or hard gel capsule. As the N-Acetyl Methyl GABA has a solvent-like nature, to place it in a soft gel or hard gel, it is preferably formulated with a surfactant to thicken and smooth out the viscosity. In an embodiment, 30-75% (w/w) sodium lauroyl lactylate or sodium stearoyl lactylate is mixed with 25-70% (w/w) N-Acetyl Methyl GABA to make a clear liquid that is more viscous than N-Acetyl Methyl GABA alone. Other oils or surfactants may be used with this combination or with N-Acetyl Methyl GABA alone. Vitamin E oil (for instance 1-10% (w/w) of the composition) may be mixed with N-Acetyl Methyl GABA. Other oils such as safflower oil, sunflower oil, soy oil, jojoba oil, other vegetable oils, may be used at applicable levels for instance with the sodium lauroyl lactylate. Other lactylates may be used, such as sodium stearoyl lactylate. In an embodiment, compositions of this invention may be prepared according to methods generally known in the art. In an embodiment, 400 mg N-Acetyl Methyl GABA may be placed with 400 mg sodium lauroyl lactylate or sodium stearoyl lactylate and filled into an 800 mg soft gelatin capsule using a capsule manufacturing machine.

In another embodiment, a hard gelatin capsule with thicker walls is used. A seal is placed around the capsule to close and seal the N-Acetyl Methyl GABA (alone or in combination with surfactants, oils, and/or other ingredients) in the capsule. In an embodiment, a 50/50 (w/w) solution of N-Acetyl Methyl GABA is placed in a single 0 capsule and filled with about 550 mg of solution for a dose level of 275 mg N-Acetyl Methyl GABA per capsule. In double 00 capsules, the fill weight may be about 800 mg total of such a mixture, including about 400 mg N-Acetyl Methyl GABA per dose unit capsule.

"Administering", "administer" and the like according to the present invention refers to providing a composition of the present invention to a subject so that the N-Acetyl Methyl GABA (or its metabolites or other components) reaches the subject's bloodstream and tissues including brain tissue and acts to aid sleep, reduce anxiety, treat insomnia, and otherwise as described throughout this application, without being bound by theory. Administration may be by the subject (self-administration) or by another. Administration to the subject may be oral, for instance in the form of a supplement such as a dietary supplement. Administration may be for instance in a solid dosage form, such as a powdered form, or a liquid or semi-liquid form, such as an oil, emulsion, gel, aqueous mixture, suspension, and the like. In an embodiment, administration may be as a discrete dose unit, for instance encapsulated in a capsule; and/or in a liquid or other form that may be for instance poured or scooped from a bottle, for instance in a 1-2 teaspoon dose. Administration may also be through parenteral, intramuscular, transdermal, topical, sublingual, intravenous, and other physiologically acceptable routes.

"Coadministration" and the like according to this invention refers to administering N-Acetyl Methyl GABA and another drug to a subject, for instance to further enhance or improve their effects. In an embodiment, a sleep agent such as melatonin is administered with N-Acetyl Methyl GABA in a composition to further improve sleep quality and other overnight characteristics of the drug. In an embodiment, N-Acetyl Methyl GABA and melatonin act synergistically to improve qualities and reduce symptoms in a subject. In an embodiment, the N-Acetyl Methyl GABA and additional drug such as melatonin are formulated together in the same composition. In an embodiment, an N-Acetyl Methyl GABA composition and a composition comprising another drug such as melatonin are administered within a time period allowing them to exert combined effects such as over sleep.

A "subject" according to the present invention is a mammal, such as a human, dog, cat, or horse. In an embodiment, a subject is a human. In an embodiment, a human subject is an adult female, an adult male, and/or a female or male child. A subject may be referred to as a patient.

"Stress" according to the present invention is a feeling of emotional or physical tension, resulting for instance from an event or thought that makes a subject feel frustrated, angry, or nervous. Stress is caused by pressure on a subject to perform, changes and in particular substantial changes to a subject's environment, and/or fear or worry about an event outcome. Stress may be caused for instance by not having enough pressure to perform or challenge in a subject's life. "Anxiety" may be a feeling of fear or apprehension about a current situation or upcoming event, and may be caused by stress. A subject may rate his or her feelings of stress or anxiety on a scale of 1 to 5, for instance where 1 is Very Poor (feeling very stressed and/or anxious), 2 is Poor, 3 is Fair, 4 is Good, and 5 is Excellent (feeling relaxed and with little to no stress or anxiety).

"Sleep quality" according to the present invention refers to how well a subject slept. In an embodiment, a subject or objective observer/device associated with the subject may rate sleep quality by selecting a number from 1 to 5, where 1 is Very Poor (interrupted sleep), 2 is Poor, 3 is Fair, 4 is Good, and 5 is Excellent ("sound", uninterrupted sleep). Sleep quality may be measured for instance by a test administered by a professional medical provider or an at-home measurement for instance of sleep quality parameters by a device, including for instance a cell phone with an application ("app") for measuring and analyzing a subject's sleep patterns. Sleep quality may also be measured by a subject's experience, as reported by the subject. Good to Excellent sleep quality may be measured for instance as sleeping for instance at least 80% of the total time in bed (good), or at least 85% of the total time (excellent, including 90, 95%, about 100%), or sleeping for more time in bed after administration of N-Acetyl Methyl GABA than before, preferably statistically significantly more time; falling asleep for instance in 30 minutes or less; having uninterrupted sleep such as not waking at all during time in bed or only waking 1 time; after falling asleep and beginning a sleep period, being awake during the sleep period for not more than 15 minutes (excellent) or not more than 30 minutes (good); and/or increasing the duration of the sleep period duration overall. Improving sleep quality according to this invention may refer to increasing a sleep quality rating number after administration of N-Acetyl Methyl GABA compared with sleep quality reported prior to administration of N-Acetyl Methyl GABA, for instance from a 2 to a 4. In an embodiment, good or excellent sleep quality, or improving sleep quality, refers to reducing excessive sleep to a more normal sleep period.

A "sleep period" or "period of sleep" according to the present invention refers to sleeping for a typical overnight period (for instance a range of 6-10 hours, or 7-9 hours, or 7.5-8.5 hours, or about 8 hours, or similar range), or for a period of time, for instance, at least 15 minutes, at least 30 minutes, at least 45 minutes, at least 1 hour, at least 2 hours, at least 3 hours, at least 4 hours, at least 5 hours, at least 6 hours, at least 7 hours, at least 8 hours, at least 9 hours, or at least 10 hours; and any range of any of these periods, for instance from 15 minutes to 10 hours. In an embodiment, a sleep period may be longer than indicated above, for instance up to 11 hours or up to 12 hours. Reference to "in bed" is to a place for the subject to sleep upon (bed, sofa, cushions, and so forth for instance for a human subject), preferably in a prostrate/lying down position but including a sitting or reclined position. References to "overnight" may be to a sleep period during nighttime for the subject, or to a different time period during the day, for instance as experienced by third shift workers.

A "good" or "excellent" period of sleep in a subject according to the present invention refers to a period of sleep for instance rated as good or excellent by the subject and/or by an objective rating such as by a device or observer. In an embodiment, a good or excellent period of sleep may include having improved sleep quality over a prior sleep period; as well as good or excellent, and/or improved, restfulness/wakefulness; good or excellent, and/or improved, mental clarity/memory; good or excellent, and/or improved, mood; and/or good or excellent, or improved, reduction of inflammation and/or pain, after the sleep period.

"Restfulness/Wakefulness" according to the present invention refers to a subject's report of how well-rested, awake, and/or energetic the subject felt after a sleep period, for instance by selecting a number from 1 to 5, where 1 is Very Poor (Groggy/Slow to Respond/Sleepy), 2 is Poor, 3 is Fair, 4 is Good, and 5 is Excellent (Wide Awake/Energetic). In an embodiment, the report may be by observation by an observer, such as a device or person including for instance a medical observer. Improving restfulness/wakefulness according to this invention refers to increasing the selected number, for instance from a 1 to a 3, when N-Acetyl Methyl GABA is administered in an effective amount prior to sleeping. Achieving good or excellent restfulness/wakefulness refers to a subject that feels rested, awake, and/or energetic after sleeping; in contrast to feeling for instance groggy, sleepy, lethargic. In an embodiment, the administration of an effective amount of N-Acetyl Methyl GABA according to this invention may also improve restfulness and/or wakefulness with or without a period of sleep.

"Mental Clarity/Memory" according to the present invention refers to a subject's report on his or her ability to focus on important matters, and/or recall immediate tasks at hand, for instance by selecting a number from 1 to 5, where 1 is Very Poor (Confused/Unfocused/Unable to Concentrate), 2 is Poor, 3 is Fair, 4 is Good, and 5 is Excellent (Clear/Focused/Able to Concentrate). an embodiment, the report may be by observation by an observer, such as a device or person including for instance a medical observer. Improving mental clarity/memory according to this invention refers to increasing the selected number, for instance from a 3 to a 4, when N-Acetyl Methyl GABA is administered in an effective amount prior to sleeping. Achieving good or excellent mental clarity/memory refers to a subject that feels alert and able to focus on tasks at hand. In an embodiment, the administration of an effective amount of N-Acetyl Methyl GABA according to this invention may also reduce anxiety and/or improve a subject's mental clarity with or without a period of sleep.

"Mood" according to the present invention refers to a subject's report of the subject's perceived emotional state for instance after a period of sleep, for instance a number from 1 to 5, where 1 is Very Poor (Irritable or sad/depressed), 2 is Poor, 3 is Fair, 4 is Good, and 5 is Excellent (Happy/Serene). an embodiment, the report may be by observation by an observer, such as a device or person including for instance a medical observer. Improving mood according to this invention refers to increasing the selected number, for instance from a 2 (poor mood) to a 3 (fair mood), when N-Acetyl Methyl GABA is administered in an effective amount prior to sleeping. Achieving a good or excellent mood refers to a subject that feels happy and satisfied after a period of sleep, for instance and preferably an overnight sleep. In an embodiment, the administration of an effective amount of N-Acetyl Methyl GABA according to this invention may reduce irritability and/or improve a subject's mood with or without a period of sleep.

"Inflammation and Pain Reduction", "Body Aches and Pains", and the like refers to inflammatory processes of the body and pain or discomfort associated with them. Inflammatory processes of the body may be reduced during sleep, and in particular during good or excellent sleep. Reduction of inflammation and pain may be rated by the subject or associated device as existing and/or reduced for instance as 1 (most inflammation and pain), 2 (inflamed and painful), 3 (somewhat inflamed and painful), 4 (little inflammation and pain), 5 (almost no or no inflammation and pain). In an embodiment, the report may be by observation by an observer, such as a device or person including for instance a medical observer. In an embodiment, reducing inflammation and pain in a subject relates to an increase in the number selected to rate inflammation and pain. In an embodiment, the administration of an effective amount of N-Acetyl Methyl GABA according to this invention may also reduce stress, reduce inflammation, and/or reduce pain with or without a period of sleep.

"Insomnia" according to the present invention refers to an inadequate sleep period such as an overnight sleep period, with the subject waking with tiredness, lack of energy, difficulty concentrating, irritable mood, and so forth, for instance as indicated above in the "Very Poor" or "Poor" categories of Sleep Quality, Restfulness/Wakefulness, Mental Clarity/Memory, and/or Mood. an embodiment, the report may be by observation by an observer, such as a device or person including for instance a medical observer. In an embodiment, insomnia refers to poor sleep quality such as difficulty falling asleep, interrupted sleep/waking frequently during the night, difficulty (e.g inability or lengthy time period) returning to sleep, waking too early, and/or unrefreshing sleep. In an embodiment, insomnia is treated with N-Acetyl Methyl GABA according to the present invention by improving one or more aspect of poor sleep quality. Such improvement may be measured by a rating system for instance of 1 to 5 as discussed above. In an embodiment, insomnia is temporary or situational insomnia. In an embodiment, insomnia according to this invention is chronic insomnia.

"Daytime Energy" according to the present invention may be measured by a subject's rating on a scale of 1 to 5 of feeling for instance 1 ("Very Poor), not feeling energetic during the day), 2, 3, 4, through 5 ("Excellent", feeling energetic during the day).

The present invention may be further understood in connection with the following Examples and embodiments. The following non-limiting Examples and embodiments described throughout this application are provided to illustrate the invention. Generally, chemical steps may be performed in any order, unless indicated otherwise.

EXAMPLES

Example 1—Synthesis and Purification of N-Acetyl Methyl GABA

Example 1 shows how to provide high yield, easily separable, N-Acetyl Methyl GABA according to the present invention, in a fairly pure state. Step 2 in particular was difficult to develop. Most acetylations using acetyl chloride use pyridine as a solvent and use trimethylamine and sodium acetate as bases. Two problems arose with these conditions. One, the yield was very low (about 5%). The second problem was in trying to extract the desired finished product from the pyridine. Di-ethyl ether extraction of acidified pyridine in water resulted in a low yield, and the residual pyridine which is very unpleasant to smell was not removed. CARTER et al., "1. Azlactones: III. Acylation of Amino Acids in Pyridine" J. Biol. Chem. 138:619-626 (1941).

The next method used a brine solution with sodium acetate and trimethylamine. The acetylation was performed with 50% acetyl chloride in acetone. After reaction, it was acidified with HCl and neutralized with trimethylamine, then extracted with 2 volumes of methylene chloride. After drying under vacuum, the yield was only 10% product, and tan in color, which indicated it was not pure. BASU et al., "Efficient acetylation of primary amines and amino acids in environmentally benign brine solution using acetyl chloride" J. Chemical Sci. 125(3):607-613 (2013).

Next, iodine crystals were tried, as disclosed by PHUKAN et al., "Mild and Useful Method for N-Acylation of Amines" Synthet. Comms. 39(15):2694-2701 (2009). The need to add sodium thiosulfate to neutralize the iodine was messy. Also, an extraction step was needed, which lowered the yield, and required a solvent that would have to be distilled to be recovered.

Next, acetylation was carried out using acetyl chloride in various solvents: DMF, DMSO, methylene chloride, acetonitrile, and ethyl acetate. The problem with this method was that the potassium carbonate was not always soluble to react properly and the solvents used had negative side effects and blocked recovery. Recovery would be difficult because the ester being prepared is like a solvent, and trying to extract it with a solvent, trying to either dry it under vacuum or distillation, was difficult. The boiling point of N-Acetyl Methyl GABA is about 65° C., and difficult to separate from solvents with a similar boiling point. DARSI et al., "Studies on N-acetylation of Anilines with Acetyl Chloride using Phase Transfer Catalysts in Different Solvents" Der Pharma Chemica 3(5):35-38 (2011).

After attempting the above methods and reviewing many others, two factors became important for a preferred method of the present invention. (1) A basic or neutral pH (preferably within a pH range of 6.5-8) needs to be maintained for the acetylation reaction work well. (2) A solvent which works and has a lower boiling point than N-Acetyl Methyl GABA is necessary, and preferably is inexpensive. The solvent should be safe to handle and to recover. In an embodiment, acetone is a solvent useful in step (2) of this invention.

Synthesis Reagents:
- GABA was supplied by Stryka Botannics, 279 Homestead Road, Hillsborough, NJ 08844, USA
- HPLC Grade Methanol, Catalog #33900HPLC, was provided by Greenfield Global, 58 Vale Road, Brookfield, CT 06804, USA
- HPLC Grade Acetone, Catalog #9003-03, Mallinckrodt-Baker Inc., Phillipsburg, NJ 08865, USA
- Hydrogen Chloride Anhydrous GAS Catalog #UN1050, Praxair Inc. Danbury CT 06810-6266, USA
- Acetyl Chloride 98%, Thermo Fisher Scientific, Shore Road, Port of Heysham, Lancashire, LA32KY, UK
- Sodium Bicarbonate USP Grade #1, VITUSA Products, 343 Snyder Ave., Berkeley Heights, NJ 07922 USA Synthesis Steps 1-3 below must be performed in order.

Step 1: Synthesis of Methyl GABA

In this step, the polar carboxyl (—C(O)OH) end of GABA ($NH_2CH_2CH_2CH_2C(O)OH$) was methylated to become —C(O)OCH$_3$ ("Methyl GABA" $NH_2CH_2CH_2CH_2C(O)OCH_3$), as follows:

GABA (300 grams) was added to 10 volumes of reagent methanol (3000 ml) in a boiling flask and then in a fume hood. Preferably, there is about 10 times the amount of methanol in order to bring the GABA into solution. Smaller amounts were tried but the yield was lower. Anhydrous HCl was bubbled in the mixture while stirring until the GABA was completely in solution. Boiling chips were added. The solution was refluxed overnight using a condenser at the boiling point of methanol (64.7° C.). The methanol was distilled off. A yield of nearly 100% Methyl GABA was achieved based on theoretical weight.

Step 2: Synthesis of N-Acetyl Methyl GABA

In this step, the polar amino (—NH$_2$) end of Methyl GABA is acetylated to become —NH—C(O)CH$_3$ ("N-Acetyl Methyl GABA"). The Methyl GABA is a clear viscous syrup in nearly 100% yield. This was determined by yield weight.

The remaining viscous liquid was poured into a 5000 mL beaker while still warm. 3000 mL of acetone was added and stirred. Then 631 grams sodium bicarbonate was added, a small scoop at a time to prevent the reaction from producing too much carbon dioxide and overflowing the beaker. This step removes the HCL from the GABA so that the reaction may proceed. Sodium bicarbonate was used to maintain the pH range between 6.5-8. The beaker was placed on a magnetic stirrer. An extraction funnel (500 mL) with 338 g (307 mL) acetyl chloride was put in place to add the acetyl chloride drop-wise to the mixture in the beaker.

Normally, acetyl chloride reactions tend to be violent and exothermic, but this reaction is calm and predictable. Without being bound by theory, the sodium bicarbonate is solubilized by the water that is produced by the reaction which reacts with the HCl attached to the amino group of the Methyl GABA. This opens up the site so the acetyl group can attach itself to the Methyl GABA. The freed HCl then reacts with the bicarbonate to form sodium chloride or salt and the $CO_2$ comes off as a gas. The solution warmed to about 40° C. during the process and bubbles formed on the top and then dissipated. The solution was covered and allowed to stir for 4 hours or until the reaction ceased. The salt was filtered from the solution and the filtrate was placed in a clean 5000 mL boiling flask and boiling stones added. The acetone was boiled off from 52° C. to 60° C. and then the N-Acetyl Methyl GABA was distilled off in clear, nearly pure form into a 2000 mL boiling flask. The solution was collected up to 78° C. The yield was about 440 g of a theoretical total of 515 g (85%). This crude distillate was about 95% pure N-Acetyl Methyl GABA by gas chromatograph (0.2 ul actual injection volume, Agilent, Santa Clara, CA), as shown in the gas chromatogram represented in FIG. 1. The second peak that elutes (2.385) is N-Acetyl Methyl GABA at about 95%.

TABLE 1

FT-IR Scan Area Percentage Report

| Peak | Peak Retention Time (min) | Type | Width (min) | Area (pA*s) | Area (%) |
|---|---|---|---|---|---|
| 1 | 1.722 | BB S | 0.0246 | 1.38594e4 | 3.30003 |
| 2 | 2.385 | VB S | 0.0433 | 3.99239e5 | 95.06185 |
| 3 | 2.628 | BV T | 0.0433 | 6879.74023 | 1.63812 |
| 4 | 8.177 | | 0.0000 | 0.00000 | 0.00000 |
| 5 | 8.972 | | 0.0000 | 0.00000 | 0.00000 |
| 6 | 9.955 | | 0.0000 | 0.00000 | 0.00000 |
| | | | | TOTAL: 4.19978e5 | |

Step 3: Purification of N-Acetyl Methyl GABA

Figure 2:
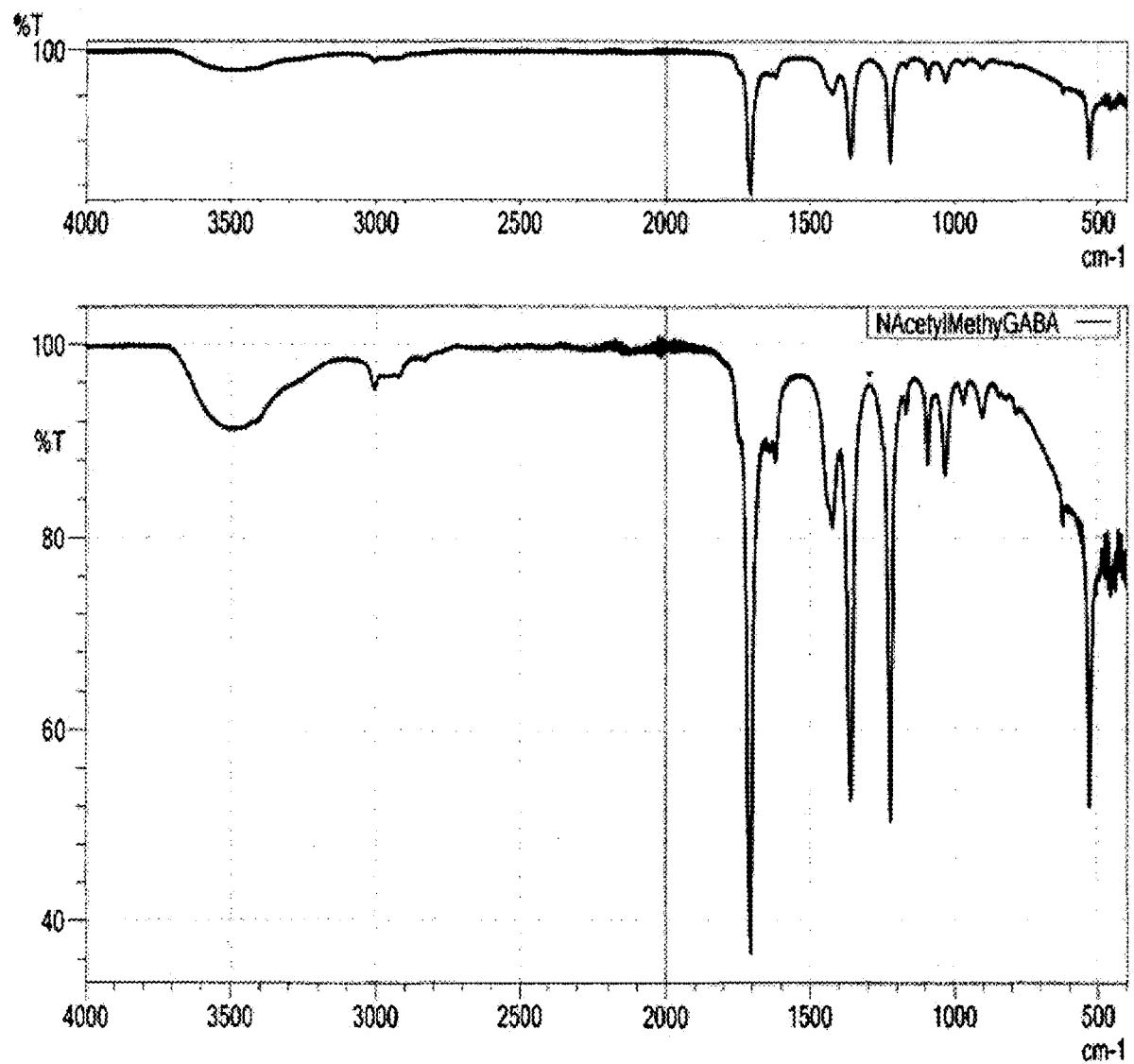
FIG. 2 represents an FT-IR scan of nearly 100% pure N-Acetyl Methyl GABA of this invention after purification of an N-Acetyl Methyl GABA distillate by a high purity distillation unit.

The crude distillate of Step 2 was applied to a high purity distillation unit to yield nearly 100% N-Acetyl Methyl GABA, as shown in FT-IR (Fourier-Transform Infrared Spectroscopy) (Shimadzu IRTracer-100, Shimadzu Scientific Instruments, Columbia, MD) scan of FIG. 2 (data in Table 1). The FT-IR scan shows expected energy bands and very little noise denoting nearly pure product. N-Acetyl Methyl GABA is a clear liquid and it has a distinct odor slightly different from ethyl acetate. Acetone and methanol can be recovered. Only a small residual solvent needs to be discarded.

Example 2

In Vivo Studies

Table 2 reports a human female subject's sleep quality, restfulness/wakefulness, mental clarity/memory, mood, and inflammation and pain reduction after 18 overnight sleep periods over the span of 15 weeks (October-January, as shown in Table 2), with 15 of the 18 nights occurring before the first administration of N-Acetyl Methyl GABA to the subject. Table 3 reports the subject's sleep quality and other parameters after self-administering 300 mg of N-Acetyl Methyl GABA before an overnight sleep period, 40 times over the span of 9 weeks (November-January, as shown in Table 3). Data in Tables 2 and 3 are based on a rating of sleep quality and other parameters from 1 to 5, where 1 is Very Poor, 2 is Poor, 3 is Fair, 4 is Good, and 5 is Excellent. Each morning after waking, the subject reported on the sleep quality, restfulness/wakefulness, mental clarity/memory, mood, and inflammation and pain reduction they felt, and/or with regard to sleep quality, used information from a "Sleep Cycle" app on a cell phone (Sleep Cycle, www.sleepcycle.com, Gothenburg, Sweden).

TABLE 2

Subject report on overnight sleep with no administration of N-Acetyl Methyl GABA (NAMGABA)

| | NAMGABA Administered? | Sleep Quality | Restfulness/ Wakefulness | Mental Clarity/Memory | Mood | Antinflammatory Action (decrease in pain) |
|---|---|---|---|---|---|---|
| Oct. 13, 19 | No NAMGABA | 1 | 1 | 2 | 1 | 1 |
| Oct. 14, 19 | No NAMGABA | 2 | 1 | 2 | 2 | 2 |
| Oct. 15, 19 | No NAMGABA | 3 | 2 | 2 | 2 | 2 |
| Oct. 18, 19 | No NAMGABA | 2 | 1 | 2 | 1 | 2 |
| Oct. 21, 20 | No NAMGABA | 2 | 2 | 2 | 2 | 2 |
| Oct. 22, 19 | No NAMGABA | 2 | 1 | 2 | 2 | 2 |
| Oct. 23, 19 | No NAMGABA | 3 | 2 | 3 | 2 | 2 |
| Oct. 29, 19 | No NAMGABA | 2 | 2 | 3 | 1 | 1 |
| Oct. 31, 19 | No NAMGABA | 1 | 1 | 2 | 1 | 1 |
| Nov. 3, 19 | No NAMGABA | 3 | 2 | 2 | 2 | 1 |
| Nov. 4, 19 | No NAMGABA | 2 | 3 | 2 | 2 | 2 |
| Nov. 10, 19 | No NAMGABA | 3 | 2 | 2 | 3 | 2 |
| Nov. 17, 19 | No NAMGABA | 2 | 1 | 2 | 3 | 1 |
| Nov. 18, 19 | No NAMGABA | 2 | 2 | 2 | 3 | 2 |
| Nov. 19, 19 | No NAMGABA | 1 | 2 | 2 | 1 | 1 |
| Nov. 26, 19 | No NAMGABA | 3 | 3 | 2 | 2 | 2 |
| Jan. 17, 20 | No NAMGABA | 3 | 4 | 2 | 2 | 3 |
| Jan. 26, 20 | No NAMGABA | 3 | 4 | 3 | 3 | 3 |
| Total Score 18 Days | | 40 | 36 | 39 | 35 | 32 |
| Average without taking N-Acetyl Methyl GABA | | 2.2 | 2 | 2.2 | 1.9 | 1.7 |

1: Very Poor
2: Poor
3: Fair
4: Good
5: Excellent

TABLE 3

Subject report on overnight sleep after administration of N-Acetyl Methyl GABA

| | Sleep Quality | Restfulness/ Wakefulness | Mental Clarity/ Memory | Mood | Antinflammatory Action (decrease in pain) |
|---|---|---|---|---|---|
| Nov. 20, 2020 | 5 | 4 | 4 | 4 | 2 |
| Nov. 21, 2019 | 4 | 3 | 3 | 3 | 3 |
| Nov. 24, 2019 | 5 | 4 | 4 | 4 | 3 |
| Nov. 25, 2019 | 5 | 4 | 4 | 4 | 4 |
| Dec. 1, 2019 | 5 | 4 | 4 | 3 | 2 |
| Dec. 2, 2019 | 5 | 4 | 4 | 4 | 3 |
| Dec. 4, 2019 | 5 | 5 | 4 | 4 | 3 |
| Dec. 5, 2019 | 5 | 5 | 4 | 3 | 2 |
| Dec. 8, 2019 | 4 | 5 | 5 | 4 | 3 |
| Dec. 9, 2019 | 5 | 5 | 5 | 4 | 3 |
| Dec. 11, 2019 | 5 | 5 | 5 | 5 | 4 |
| Dec. 15, 2019 | 5 | 5 | 5 | 4 | 3 |
| Dec. 16, 2019 | 4 | 4 | 4 | 5 | 4 |
| Dec. 17, 2019 | 5 | 5 | 5 | 5 | 4 |
| Dec. 18, 2019 | 5 | 5 | 5 | 5 | 4 |
| Dec. 20, 2019 | 5 | 5 | 5 | 5 | 4 |
| Dec. 25, 2019 | 5 | 5 | 5 | 4 | 4 |
| Dec. 26, 2019 | 5 | 5 | 5 | 5 | 4 |
| Dec. 28, 2019 | 4 | 5 | 5 | 5 | 4 |
| Dec. 29, 2019 | 5 | 5 | 4 | 5 | 4 |
| Dec. 30, 2019 | 4 | 4 | 4 | 5 | 4 |
| Jan. 1, 2020 | 4 | 4 | 5 | 5 | 4 |
| Jan. 2, 2020 | 5 | 5 | 4 | 4 | 4 |
| Jan. 4, 2020 | 5 | 5 | 4 | 5 | 4 |
| Jan. 5, 2020 | 5 | 5 | 4 | 5 | 5 |
| Jan. 6, 2020 | 5 | 5 | 5 | 5 | 5 |
| Jan. 7, 2020 | 4 | 4 | 4 | 5 | 4 |
| Jan. 8, 2020 | 5 | 4 | 4 | 5 | 4 |
| Jan. 9, 2020 | 4 | 4 | 5 | 5 | 5 |
| Jan. 11, 2020 | 5 | 5 | 4 | 5 | 5 |
| Jan. 12, 2020 | 5 | 5 | 4 | 5 | 5 |
| Jan. 13, 2020 | 5 | 4 | 4 | 3 | 3 |
| Jan. 14, 2020 | 5 | 4 | 5 | 4 | 4 |
| Jan. 15, 2020 | 5 | 4 | 4 | 4 | 4 |
| Jan. 16, 2020 | 5 | 5 | 5 | 4 | 4 |
| Jan. 19, 2020 | 5 | 5 | 4 | 4 | 4 |
| Jan. 20, 2020 | 4 | 4 | 4 | 4 | 4 |
| Jan. 21, 2020 | 4 | 5 | 5 | 5 | 5 |
| Jan. 22, 2020 | 5 | 5 | 5 | 4 | 4 |
| Jan. 23, 2020 | 5 | 5 | 5 | 5 | 5 |
| Total Score, 40 days | 190 | 183 | 177 | 176 | 153 |
| Average With N-Acetyl Methyl GABA | 4.7 | 4.6 | 4.4 | 4.4 | 3.8 |

1: Very Poor
2: Poor
3: Fair
4: Good
5: Excellent

TABLE 4

Summary of subject reports before and after administration of N-Acetyl Methyl GABA

| | Sleep Quality | Restfulness/ Wakefulness | Mental Clarity/ Memory | Mood | Anti-inflammatory Action (decrease in pain) |
|---|---|---|---|---|---|
| Without N-Acetyl Methyl GABA, average score | 2.2 | 2 | 2.2 | 1.9 | 1.7 |
| With N-Acetyl Methyl GABA, average score | 4.7 | 4.6 | 4.4 | 4.4 | 3.8 |
| Improvement after taking N-Acetyl Methyl GABA | +2.5 | +2.6 | +2.2 | +2.5 | +2.1 |

1: Very Poor
2: Poor
3: Fair
4: Good
5: Excellent

Discussion:

The subject of Example 2 reported improved sleep quality and other tested parameters after self-administration of N-Acetyl Methyl GABA prior to an overnight sleep period. For 14 of the days reported in Table 2, before the first administration of N-Acetyl Methyl GABA, data is from a sleep app on a cell phone device. Other data in Table 2 is from the subject's experience as reported for a given sleep period. The data before first administration of N-Acetyl Methyl GABA provides a baseline of sleep patterns for the subject with no sleep aid. The average sleep quality in the subject before a first administration of N-Acetyl Methyl GABA was 73.8%. The average percentage of sleep quality improved after administration of N-Acetyl Methyl GABA according to this invention, with average sleep quality at 80.4%. The subject also reported no longer feeling morning or mid-afternoon anxiety, and having better mental clarity and clearer focus, after waking from the sleep periods. No side effects from the administration of N-Acetyl Methyl GABA were reported by the subject.

Table 4 represents average data from Tables 2 and 3, and provides an improvement score for parameters studied after taking N-Acetyl Methyl GABA. As shown in Table 4, sleep quality during overnight sleep periods for the subject without N-Acetyl Methyl GABA was on average 2.2, or "Poor" to "Fair" on average. After taking N-Acetyl Methyl GABA, sleep quality during overnight sleep periods for the subject was on average 4.7, or "Good" to "Excellent". On average, sleep quality for the subject improved by 2.5, or approximately 115% (2.5/2.2*100%).

The subject's restfulness/wakefulness was rated on a scale of 1 to 5 as discussed above, after an overnight sleep period with no administration of N-Acetyl Methyl GABA (Table 2) and with administration of N-Acetyl Methyl GABA (Table 3). As shown in Table 4, the subject rated restfulness/ wakefulness after sleep periods without N-Acetyl Methyl GABA as 2, "Poor", on average; with N-Acetyl Methyl GABA, restfulness/wakefulness was rated at 4.6, or "Good" to "Excellent". On average, restfulness/wakefulness after sleep periods with N-Acetyl Methyl GABA improved by 2.6 on the rating scale, or 130% (2.6/2*100%).

The subject's mental clarity/memory was rated on a scale of 1 to 5 as discussed above, after an overnight sleep period with no administration of N-Acetyl Methyl GABA (Table 2) and with administration of N-Acetyl Methyl GABA (Table 3). As shown in Table 4, on average the subject rated mental clarity/memory after sleep periods without N-Acetyl Methyl GABA as 2.2, "Poor" to "Fair"; with N-Acetyl Methyl GABA, mental clarity/memory was rated at 4.4, or "Good" to "Excellent". On average, mental clarity/memory after sleep periods with N-Acetyl Methyl GABA improved by 2.2 on the rating scale, or by 100% (2.2/2.2*100%).

The subject's mood was rated on a scale of 1 to 5 as discussed above, after an overnight sleep period with no administration of N-Acetyl Methyl GABA (Table 2) and with administration of N-Acetyl Methyl GABA (Table 3). As shown in Table 4, on average the subject rated mood after sleep periods without N-Acetyl Methyl GABA as 1.9, "Very Poor" to "Poor"; with N-Acetyl Methyl GABA, the subject's mood rated at 4.4, or "Good" to "Excellent". On average, the subject's mood after sleep periods with N-Acetyl Methyl GABA improved by 2.5 on the rating scale, or by about 132% (2.5/1.9*100%).

Before administration of N-Acetyl Methyl GABA, the subject reported higher levels of inflammatory conditions on a daily basis, and consequent pain/discomfort. The subject's inflammation/pain was rated on a scale of 1 to 5 as discussed above, after an overnight sleep period with no administration of N-Acetyl Methyl GABA (Table 2) and with administration of N-Acetyl Methyl GABA (Table 3). As shown in Table 4, on average the subject rated inflammation/pain after sleep periods without N-Acetyl Methyl GABA as 1.7, "Very Poor" to "Poor". With N-Acetyl Methyl GABA, the subject's inflammation/pain rated at 3.8, or "Fair" to "Good". On average, the subject's inflammation/pain after sleep periods with N-Acetyl Methyl GABA improved by 2.1 on the rating scale, or by about 125% (2.1/1.7*100%).

The administration of N-Acetyl Methyl GABA to other human subjects according to this invention has been well tolerated to date. Subjects report improved sleep quality when N-Acetyl Methyl GABA is administered prior to a sleep period, and next day, improved memory and mental clarity, improved restfulness and well-being, improved mood, and decreased inflammation and pain. Subjects report more natural sleep without the morning grogginess associated with many sleep aids. Subjects report they slept all night long without waking. Subjects report that general body inflammation and aches and pains were also reduced when N-Acetyl Methyl GABA was administered prior to an overnight sleep period. Subjects report the mind is clear and the attitude is positive after N-Acetyl Methyl GABA was administered prior to an overnight sleep period. Without being bound by theory, this may be due to anxiolytic effects of N-Acetyl Methyl GABA.

Example 3

An embodiment of an emulsion of a liposome that may be provided for administration according to this invention is set out in Table 5, below.

TABLE 5

N-Acetyl Methyl GABA Composition

| Ingredient | MG, IU, ML added | % composition (w/w) |
|---|---|---|
| Deionized Water | 5595.0 ml | 70.0% |
| Glycerine USP | 1162.0 ml | 14.5% |
| Soy Lecithin Liquid | 565.0 ml | 7.1% |

TABLE 5-continued

N-Acetyl Methyl GABA Composition

| Ingredient | MG, IU, ML added | % composition (w/w) |
|---|---|---|
| N-Acetyl Methyl GABA | 300.0 mg | 3.8% |
| Orange Flavor Liquid | 100.0 ml | 1.3% |
| Sodium Lauroyl Lactylate | 80.0 mg | 1.0% |
| Stevia Extract 90% | 30.0 ml | 0.38% |
| Bitter Mask Powder | 28.0 mg | 0.35% |
| Luo Han Guo 50% | 28.0 ml | 0.35% |
| Guar Gum (Cosmetic Grade) | 25.0 mg | 0.31% |
| Potassium Sorbate (Granular) | 22.0 mg | 0.28% |
| Curcumin 95% | 20.0 ml | 0.25% |
| Vitamin E Oil | 18.0 ml | 0.22% |
| Peppermint Oil | 10.0 ml | 0.125% |
| Cinnamon (Cassia) Oil | 10.0 ml | 0.125% |
| Melatonin | 5.0 mg | 0.06% |
| DOSE WEIGHT | 7.998 g | TOTAL: 100% (rounded) |

The above composition of the present invention is preferably shaken well before administration. The composition is for oral administration. In an embodiment, the composition promotes healthy sleep, helps manage stress and anxiousness, and may be taken for instance 30 minutes before bedtime (i.e. an overnight sleep period). Active ingredient similar to ethyl acetate, which can be difficult to mask, and is preferably masked for instance as in the composition discussed above. Strong flavors are preferred accordingly in compositions of the present invention.

Examples 4 and 5

Study Purpose:

The purpose of this study was to quantify the effectiveness of N-Acetyl Methyl GABA with sleep and related symptoms and qualities. Without being bound by theory, it is believed that standard GABA cannot cross the blood brain barrier. N-Acetyl Methyl GABA is believed to cross the blood brain barrier and act directly upon the CNS.

N-Acetyl Methyl GABA Composition:

The composition described in Table 6 was taken orally by each patient once daily before an overnight sleep period.

TABLE 6

N-Acetyl Methyl GABA composition

| RM# | TYPE | INGREDIENT | MGS-IU-ML | ACT | % OV | GMS-ML | % COMPOSITION (W/W) |
|---|---|---|---|---|---|---|---|
| 212 | A | DEIONIZED WATER | 4970.0 | 1.00 | 0 | 4.9700 | 62.1% |
| 209 | A | GLYCERINE USP | 1181.0 | 1.00 | 0 | 1.1810 | 14.8% |
| 3540 | A | MCT OIL 60/40 | 465.0 | 1.00 | 0 | 0.4650 | 5.8% |
| 2707 | A | A-SOY LECITHIN LIQUID | 400.0 | 1.00 | 0 | 0.4000 | 5.0% |
| 3659 | A | N-ACETYL METHYL GABA | 300.0 | 0.95 | 5 | 0.3316 | 3.8% |
| 2015 | A | ORANGE FLAVOR LIQ | 186.0 | 1.00 | 0 | 0.1860 | 2.3% |
| 1829 | A | XYLITOL GRANULAR (FINE) | 150.0 | 1.00 | 0 | 0.1500 | 1.9% |
| 3490 | A | SODIUM LAUROYL LACTYLATE | 56.0 | 1.00 | 0 | 0.0560 | 0.7% |
| 1348 | A | STEVIA EXT 90% | 46.0 | 1.00 | 0 | 0.0460 | 0.6% |
| 2108 | A | BITTER MASK POWDER 30-09 | 46.0 | 1.00 | 0 | 0.0460 | 0.6% |
| 3635 | A | LUO HAN GUO 50% | 46.0 | 1.00 | 0 | 0.0460 | 0.6% |
| 268 | A | PEPPERMINT OIL | 33.0 | 1.00 | 0 | 0.0330 | 0.4% |
| 2053 | A | GUAR GUM (COSMETIC GRADE) | 24.0 | 1.00 | 0 | 0.0240 | 0.3% |
| 384 | A | CINNAMON (CASSIA) OIL | 24.0 | 1.00 | 0 | 0.0240 | 0.3% |
| 255 | A | POTASSIUM SORBATE (GRAN) | 20.0 | 1.00 | 0 | 0.0200 | 0.25% |
| 298 | A | VITAMIN E OIL | 18.0 | 1.00 | 0 | 0.0180 | 0.23% |
| 1308 | A | MELATONIN | 5.0 | 1.00 | 0 | 0.0050 | 0.06% |
| | | DOSE WEIGHT = 8.002 GRAMS | | | | 8 g | 100% (rounded) |

N-Acetyl Methyl GABA, along with melatonin are formulated in a base of purified water, glycerine, soy lecithin, natural and artificial orange flavor, sodium lauroyl lactylate, Stevia extract, potassium sorbate (preservative), Luo Han Guo Extract, Guar gum, Curcumin extract, Vitamin E Oil, Peppermint Oil, Cinnamon Oil. In an embodiment, the ingredients combine to weight 8 g, volume approximately 2 tsp, as 1 serving size. In an embodiment, the serving size includes an effective amount of about 300 mg N-Acetyl Methyl GABA. In an embodiment, a dose of 1-2 serving sizes is taken before bedtime. In an embodiment, larger serving sizes, such as 3 or more serving sizes, may be taken by a human subject. In an embodiment, the composition has a strong cinnamon/mint flavor and very little after taste. The N-Acetyl Methyl GABA has a strong solvent like taste Study Dosage:

Subjects were administered 2 teaspoons (8 g) of the liquid N-Acetyl Methyl GABA composition described above approximately 30 minutes before going to bed.

Study Design:

Study participants: Group 1:15 subjects (human)

Group 2: 31 subjects (human)

Duration:

7 day pre-study symptomatology (no N-Acetyl Methyl GABA (NAMG) taken) to record a baseline of patient symptoms.

14 day study symptomatology (taking N-Acetyl Methyl GABA) to record patient symptoms.

Criteria for Eligibility:

Age requirements: Anyone over the age of 12 was eligible to participate in the study.

Type of Patient:

Preferred subject would have minimum two of the following symptoms prior to study: Sleep imbalance; insomnia; anxiety; mood issue; stress; mental clarity, memory and/or focus issues; daytime energy issues; body aches and pains; digestive issues; stress headaches.

Subjects were not asked to alter their normal life habits such as drinking alcohol, smoking or caffeine before going to sleep.

Medications:

Subjects were asked to not use additional natural supplements other than the N-Acetyl Methyl GABA composition for sleep during the 14 day study.

Subjects were allowed to stay on any current medications they were on, if any, and to note the medications. One Group I patient reported taking benzodiazepine during the study and was not asked to discontinue use.

All subjects reported that they did adhere to protocol.

Tables 7, 8 and 9 show patient outcomes for Groups 1 and 2. Ratings were made each day during the study period (7 days pre-administration, 14-days during N-Acetyl Methyl GABA administration), based on a scale of 1 to 5. Improvements are shown by increased ratings in qualities such as Sleep Quality, Restfulness/Wakefulness, Mental Clarity/Memory, Mood, Daytime Energy are shown for each patient in Table 7, as are reductions in symptoms such as stress, anxiety, body aches/pain, stress headaches, and digestive issues. The 5 far-right columns refer to waking and falling back asleep during an overnight sleep period. Patient gender and age for Table 7 is as follows: Patient 1 (P1): M/age 32, P2: M/28, P3: F/22; P4: F/49, P5: M/54, P6: F/32, P7: M/35, P8: M/56, P9: F/47, P10: M/38, P11: F/68, P12: F/34, P13: M/26, P14: M/44, P15: F/20. Similarly for Tables 8 and 9, improved qualities, reduced symptoms, and overnight sleep period details are shown as a percentage over baseline qualities and symptoms. Patient gender and age for Table 8 is as follows: Patient 1 (P1): M/70, P2: F/47, P3: F/69, P4: F/49, P5: M/51, P6: F/28, P7: F/66, P8: F/53, P9: M/59, P10: M/38, P11: M/31, P12: F/29, P13: M/73, P14: F/47, P15: M/56, P16: F/59, P17: M/34, P18: F/73, P19: F/62, P20: M/61, P21: F/62, P22: F/63, P23: F/62, P24: F/22, P25: M/34, P26: M/19, P27: F/27, P28: F/31, P29: M/39, P30: M/69, P31: F/47.

TABLE 7

Nighttime Study, 15 Human Patient Outcomes

| Patient # (Gender/Age) | Sleep Quality Improved (%) | Restfulness/ Wakefulness Improved (%) | Mental Clarity/ Memory Improved (%) | Mood Improved (%) | Daytime energy Improved (%) | Stress Reduced (%) | Anxiety Reduced (%) |
|---|---|---|---|---|---|---|---|
| 1 | 78 | 60 | 74 | 124 | 124 | 83 | 93 |
| 2 | 38 | 107 | 106 | 115 | 100 | 5 | 92 |
| 3 | 123 | 155 | 115 | 170 | 130 | 93 | 134 |
| 4 | 116 | 133 | 169 | 288 | 195 | 143 | 180 |
| 5 | 88 | 122 | 5 | 150 | 114 | 114 | 160 |
| 6 | 119 | 115 | 40 | 51 | 68 | 47 | 93 |
| 7 | 70 | 87 | 45 | 79 | 72 | 77 | 142 |
| 8 | 65 | 89 | 79 | 192 | 167 | 133 | 180 |
| 9 | 89 | 31 | 133 | 65 | 124 | 68 | 100 |
| 10 | 88 | 64 | 56 | 163 | 126 | 94 | 83 |
| 11 | 49 | 43 | 33 | 124 | 94 | 47 | 27 |
| 12 | 133 | 17 | 24 | 100 | 100 | 50 | 180 |
| 13 | 63 | 86 | 200 | 155 | 180 | 79 | 121 |
| 14 | 46 | 112 | 22 | 84 | 67 | 87 | 100 |
| 15 | 119 | 14 | 62 | 169 | 60 | 50 | 312 |

| Body Aches/Pain Reduced | Stress Headaches Reduced (%) | Digestive Issues Reduced (%) | Waking (overall) Reduced (%) | Waking (# times) Reduced (%) | Falling Back to Sleep Improved (%) | Time to Fall Back to Sleep Reduced (%) | Overall Sleep Duration Increased (%) |
|---|---|---|---|---|---|---|---|
| 87 | 100 | 59 | 245 | 934 | 100 | 540 | 19.5 |
| 72 | 124 | 44 | 245 | 245 | NA* | NA* | 29 |
| 124 | 178 | 108 | 178 | 456 | 20 | 167 | 17 |
| 210 | 113 | 76 | 376 | 376 | 376 | 968 | 25 |
| 68 | 258 | 79 | 100 | 300 | 100 | 1373 | 24 |
| 40 | 33 | 0 | 133 | 365 | NA* | NA* | 15 |
| 43 | 92 | 24 | NA* | NA* | NA* | NA* | 00 |
| 56 | 211 | 59 | 133 | 365 | 133 | 736 | 12 |
| 40 | −5 | 30 | 133 | 133 | 133 | 740 | 46 |
| 22 | 195 | 14 | 0 | 100 | 0 | 478 | 18 |
| 37 | 0 | 27 | 0 | 0 | 0 | 202 | 18 |
| −13 | 100 | 15 | 178 | 178 | 178 | 520 | 8 |
| 47 | 0 | 21 | 75 | 75 | 75 | 336 | 17 |
| 19 | 81 | 17 | 614 | 614 | NA* | NA* | 10 |
| 40 | 0 | 14 | 100 | 376 | 35 | 499 | 12 |

*Patient reported that during baseline when patient woke, could not fall back to sleep.

TABLE 8

Nighttime Study, 31 Patient Outcomes

| Patient # | Study Dates (2020) | Sleep Quality Improved (%) | Restfulness/ Wakefulness Improved (%) | Mental Clarity/ Memory Improved (%) | Mood Improved (%) | Daytime Energy Improved (%) | Stress Reduced (%) | Anxiety Reduced (%) | Body Aches/ Pain Reduced | Stress Headaches Reduced (%) | Digestive Issues Reduced (%) |
|---|---|---|---|---|---|---|---|---|---|---|---|
| 1  | 11/2-11/22  | 37  | 37  | 33  | 58  | 68  | 37  | 37  | 53  | 88  | 68 |
| 2  | 11/2-11/22  | 75  | 43  | 45  | 45  | 48  | 60  | 19  | 70  | 71  | 33 |
| 3  | 11/2-11/22  | 61  | 79  | 60  | 77  | 83  | 115 | 57  | 11  | 34  | 0 |
| 4  | 11/2-11/22  | 12  | 45  | 40  | 82  | 62  | 70  | 27  | 42  | 74  | 55 |
| 5  | 11/2-11/22  | 106 | 115 | 81  | 122 | 37  | 144 | 40  | 0   | 0   | 40 |
| 6  | 11/2-11/22  | 75  | 85  | 115 | 60  | 52  | 81  | 107 | 20  | 0   | 0 |
| 7  | 11/16-12/6  | 40  | 48  | 117 | 122 | 122 | 83  | 129 | 30  | 122 | 5 |
| 8  | 11/16-12/6  | 110 | 95  | 81  | 100 | 100 | 135 | 65  | 33  | 91  | 27 |
| 9  | 11/16-12/6  | 60  | 131 | 106 | 134 | 70  | 92  | 51  | 36  | 100 | 27 |
| 10 | 11/16-12/6  | 89  | 148 | 146 | 152 | 159 | 118 | 127 | 10  | 110 | 73 |
| 11 | 11/18-12/8  | 107 | 106 | 64  | 167 | 92  | 134 | 180 | 4   | 93  | 0 |
| 12 | 11/25-12/15 | 215 | 93  | 93  | 94  | 82  | 182 | 184 | 29  | 343 | 15 |
| 13 | 11/23-12/13 | 143 | 101 | 43  | 81  | 65  | 126 | 157 | 60  | 177 | 33 |
| 14 | 11/23-12/13 | 50  | 112 | 89  | 134 | 43  | 118 | 75  | 50  | 87  | 40 |
| 15 | 11/23-12/13 | 134 | 87  | 112 | 134 | 43  | 88  | 60  | 46  | 173 | 4 |
| 16 | 11/25-12/15 | 100 | 93  | 184 | 100 | 112 | 121 | 117 | 77  | 188 | 15 |
| 17 | 11/12-12/2  | 134 | 100 | 118 | 150 | 100 | 180 | 56  | 12  | 81  | 11 |
| 18 | 11/19-12/9  | 92  | 50  | 65  | 68  | 100 | 61  | 65  | 0   | 0   | 0 |
| 19 | 11/23-12/13 | 96  | 75  | 31  | 72  | 40  | 39  | 133 | 93  | 81  | 55 |
| 20 | 11/23-12/13 | 64  | 66  | 43  | 43  | 33  | 75  | 0   | 13  | 29  | 0 |
| 21 | 11/23-12/13 | 69  | 33  | 57  | 22  | 27  | 37  | 34  | 75  | 25  | 0 |
| 22 | 11/25-12/15 | 81  | 59  | 81  | 40  | 55  | 69  | 27  | 52  | 100 | 38 |
| 23 | 11/25-12/15 | 75  | 112 | 100 | 70  | 66  | 180 | 148 | 121 | 87  | 75 |
| 24 | 11/11-12/1  | 69  | 121 | 134 | 144 | 100 | 107 | 200 | 40  | 148 | 33 |
| 25 | 11/11-12/1  | 115 | 148 | 94  | 205 | 0   | 78  | 100 | 0   | 133 | 29 |
| 26 | 11/11-12/1  | 89  | 50  | 33  | 133 | 22  | 72  | 65  | 32  | 121 | 31 |
| 27 | 11/28-12/18 | 52  | 121 | 40  | 150 | 43  | 36  | 87  | 4   | 100 | 0 |
| 28 | 11/27-12/17 | 67  | 50  | 8   | 75  | 14  | 40  | 180 | 0   | 110 | 0 |
| 29 | 11/16-12/6  | 67  | 150 | 79  | 192 | 89  | 87  | 367 | 50  | 180 | 50 |
| 30 | 11/14-12/4  | 35  | 27  | 59  | 93  | 27  | 33  | 27  | 13  | 45  | 10 |
| 31 | 11/5-11/25  | 79  | 94  | 32  | 118 | 40  | 58  | 62  | 17  | 94  | 8 |

TABLE 9

Changes in Common Sleep Parameters in Group 2 Subjects

| Patient | Waking In Middle of Night DECREASED by (%) | Average # Times Woken in Middle of Night DECREASED by (%) | Average Baseline To Fall Back Asleep DECREASED before/during study by (min) Before NAMG | After NAMG | Average Baseline of Sleep per night before/during study(hours) Before NAMG | After NAMG |
|---|---|---|---|---|---|---|
| 1  | 100  | 300  | 22.14 | 5.64  | 5.64 | 6.39 |
| 2  | 0    | 0    | 35    | 8.57  | 5.86 | 6.32 |
| 3  | 75   | 75   | 52.86 | 14.64 | 5.79 | 6.39 |
| 4  | 0    | 0    | 30    | 16.07 | 7    | 7.61 |
| 5  | 0    | 0    | 38.57 | 17.43 | 6.64 | 7.64 |
| 6  | 0    | 0    | 49.29 | 20    | 5.5  | 6.29 |
| 7  | 100  | 200  | 6.43  | 0     | 5.64 | 6.64 |
| 8  | 41   | 41   | 0     | 0     | 6.5  | 7.18 |
| 9  | 207  | 207  | 8.57  | 0.71  | 7.29 | 7.93 |
| 10 | 56   | 56   | 35    | 10.71 | 6.07 | 7.29 |
| 11 | 307  | 514  | 21.43 | 1.43  | 6.5  | 7.61 |
| 12 | 56   | 590  | 30.71 | 3.57  | 6.86 | 7.89 |
| 13 | 27   | 27   | 15.71 | 5     | 6.5  | 7.29 |
| 14 | (NA) | (NA) | (NA)  | (NA)  | 7    | 7.79 |
| 15 | 16   | 16   | 19.29 | 6.07  | 7.5  | 8 |
| 16 | 132  | 433  | 35    | 4.29  | 7    | 7.82 |
| 17 | 178  | 217  | 27.86 | 5     | 7.14 | 7.82 |
| 18 | 0    | 77   | 30    | 11    | 7    | 7.96 |
| 19 | 0    | 286  | 51.43 | 18.21 | 6    | 6.32 |
| 20 | 178  | 456  | 25    | 3.57  | 5    | 5.96 |
| 21 | 0    | 129  | 60    | 6.79  | 6    | 6.64 |
| 22 | 0    | 146  | 53.57 | 8.93  | 5.5  | 6.89 |
| 23 | 0    | 110  | 132.86| 33.93 | 5.86 | 6.93 |
| 24 | 41   | 41   | 30    | 4.29  | 6.5  | 7 |
| 25 | 133  | 165  | 37.14 | 2.86  | 6.93 | 7.29 |
| 26 | 16   | 50   | 25.71 | 8.57  | 7    | 7.21 |
| 27 | 100  | 300  | 39.29 | 6.79  | 6.5  | 7.36 |
| 28 | 133  | 303  | 52.86 | 7.5   | 5.79 | 7.25 |
| 29 | 16   | 47   | 29.29 | 13.21 | 6    | 6.89 |
| 30 | 133  | 75   | 8.57  | 7.14  | 5.57 | 6.46 |
| 31 | 41   | 283  | 60    | 14.64 | 4.79 | 6.25 |

*Did not wake during night

**Subject reported once awake, stays awake

Table 10 shows a summary of the nighttime sleep study with an N-Acetyl Methyl GABA composition of this invention.

TABLE 10

Summary of Nighttime Study, 31 (Group 2) Human Patient Outcomes

| Type of Change | Quality/Symptom | % Change |
| --- | --- | --- |
| Increase in Quality | Sleep Quality | 84 |
| Increase in Quality | Restfulness/Wakefulness | 86 |
| Increase in Quality | Mental Clarity/Memory | 77 |
| Increase in Quality | Mood | 104 |
| Increase in Quality | Daytime Energy | 64 |
| Reduction in Symptoms | Stress | 91 |
| Reduction in Symptoms | Anxiety | 96 |
| Reduction in Symptoms | Body Aches/Pain | 35 |
| Reduction in Symptoms | Stress Headaches | 100 |
| Reduction in Symptoms | Digestive Issues | 25 |

Example 6

Daytime Study

Study Purpose:

The Purpose of this study was to quantify the effectiveness of N-Acetyl Methyl GABA on FAMMS (Fatigue, Anxiety, Mood, Mind, Stress) and related symptoms and qualities. (Mind refers to mental clarity, memory and focus).

GABA cannot cross the blood brain barrier. N-Acetyl Methyl GABA was created to provide a source of GABA that could cross the blood brain barrier and act directly upon the CNS. Having a quantified study was essential to demonstrating the effectiveness of N-Acetyl Methyl GABA.

Due to the above-described effects of N-Acetyl Methyl GABA on sleep and relaxation, a sleep quality section was added to see how a "daytime" version of N-Acetyl Methyl GABA (administered without melatonin) assisted with sleep quality for daytime patients. This was also beneficial for patients that prefer not to take melatonin.

Study Design:
  Study participants: 19 subjects
Duration:
  7 day pre-study symptomology (no N-Acetyl Methyl GABA taken) to record a baseline of patient symptoms.
  14 day study symptomology (taking N-Acetyl Methyl GABA) to record patient symptoms.

Criteria for Eligibility:
  Age requirements: Anyone over the age of 12 was eligible to participate in the study.

Type of Patient:
  Preferred subject would have minimum two of the following symptoms prior to study: FAMMS (Fatigue, Anxiety, Mood, Mind, Stress) (Mind defines mental clarity, memory and focus issues), sleep imbalance, insomnia, daytime energy issues.

Subjects were not asked to alter their normal life habits such as drinking alcohol, smoking or caffeine.

Medications:
  Subjects were asked to not use any additional mind/body stress relief or natural supplements other than the N-Acetyl Methyl GABA composition ("GabaSorb® Daytime") during the 14 day study.
  Subjects were allowed to stay on any current medications they were on, if any, as long as they were noted.
  All subjects reported that they did adhere to protocol.

Study Dosage:
  Subjects were asked to take 2 teaspoons of the liquid N-Acetyl Methyl GABA composition (Gabasorb Daytime) daily in the morning or early afternoon if they suffered from two or more symptoms listed in the protocol.
  Subjects were allowed to take the GabaSorb Daytime in the evening if their symptoms were more persistent during evening hours.
  This also allowed for patients who wish not to take melatonin to take the GabaSorb Daytime in the evening.

N-Acetyl Methyl GABA Composition:
  The N-Acetyl Methyl GABA composition described in Table 11 was taken orally by each patient once daily.

TABLE 11

N-Acetyl Methyl GABA Composition

| RM# | TYPE | INGREDIENT | MGS-IU-ML | ACT | % OV | GMS-ML | % COMPOSITION (W/W) |
| --- | --- | --- | --- | --- | --- | --- | --- |
| 212 | A | DEIONIZED WATER | 4970.0 | 1.00 | 0 | 4.9700 | 62.4% |
| 209 | A | GLYCERINE USP | 1181.0 | 1.00 | 0 | 1.1810 | 14.8% |
| 3540 | A | MCT OIL 60/40 | 465.0 | 1.00 | 0 | 0.4650 | 5.8% |
| 2707 | A | A-SOY LECITHIN LIQUID | 400.0 | 1.00 | 0 | 0.4000 | 5.0% |
| 3659 | A | N-ACETYL METHYL GABA | 300.0 | 0.95 | 5 | 0.3316 | 3.8% |
| 2015 | A | ORANGE FLAVOR LIQ | 186.0 | 1.00 | 0 | 0.1860 | 2.3% |
| 1829 | A | XYLITOL GRANULAR (FINE) | 150.0 | 1.00 | 0 | 0.1500 | 1.9% |
| 3490 | A | SODIUM LAUROYL LACTYLATE | 56.0 | 1.00 | 0 | 0.0560 | 0.7% |
| 1348 | A | STEVIA EXT 90% | 46.0 | 1.00 | 0 | 0.0460 | 0.6% |
| 2108 | A | BITTER MASK POWDER 30-09 | 46.0 | 1.00 | 0 | 0.0460 | 0.6% |
| 3635 | A | LUO HAN GUO 50% | 46.0 | 1.00 | 0 | 0.0460 | 0.6% |
| 268 | A | PEPPERMINT OIL | 33.0 | 1.00 | 0 | 0.0330 | 0.4% |
| 2053 | A | GUAR GUM (COSMETIC GRADE) | 24.0 | 1.00 | 0 | 0.0240 | 0.3% |
| 384 | A | CINNAMON (CASSIA) OIL | 24.0 | 1.00 | 0 | 0.0240 | 0.3% |
| 255 | A | POTASSIUM SORBATE (GRAN) | 20.0 | 1.00 | 0 | 0.0200 | 0.25% |
| 298 | A | VITAMIN E OIL | 18.0 | 1.00 | 0 | 0.0180 | 0.23% |
| DOSE WEIGHT = 7.965 GRAMS (approx. 8 g) | | | | | | 8 g | 100% |

Study Dosage:
  Subjects were administered 2 teaspoons (8 g) of the liquid N-Acetyl Methyl GABA composition described above.
  Table 12 shows patient outcomes for this study. Ratings were made each day during the study period (7 days pre-administration, 14-days during N-Acetyl Methyl GABA administration), based on a scale of 1 to 5. Improvements are shown by increased ratings over baseline in qualities such as Stress, Anxiety, Mental Clarity and Memory, Mood, Daytime Energy, and Sleep Quality for each patient in Table 12. Patient gender and age for Table 12 are as follows: Patient 1 (P1): M/age 80, P2: F/47, P3: F/46; P4: F/31, P5: F/19, P6: F/62, P7: M/34, P8: F/47, P9: F/29, P10: M/59, P11: M/54, P12: M/38, P13: M/56, P14: M/22, P15: F/23, P16: M/50, P17: M/19, P18: F/44, P19: F/27.

TABLE 12

Administration of N-Acetyl Methyl GABA in 19 human patients, daytime study without melatonin

| Patient # | Stress Reduced (%) | Anxiety Reduced (%) | Mental Clarity/ Memory Improved (%) | Mood Improved (%) | Daytime Energy Improved (%) | Sleep Quality Improved (%) |
|---|---|---|---|---|---|---|
| 1 | 48 | 35 | 57 | 20 | 40 | 78 |
| 2 | 45 | 32 | 55 | 94 | 32 | 95 |
| 3 | 36 | 22 | 72 | 39 | 88 | 118 |
| 4 | 33 | 40 | 43 | 68 | 88 | 150 |
| 5 | 72 | 46 | 100 | 100 | 29 | 233 |
| 6 | 17 | 107 | 82 | 100 | 57 | 62 |
| 7 | 25 | 71 | 52 | 120 | 74 | 62 |
| 8 | 40 | 126 | 56 | 152 | 36 | 77 |
| 9 | 78 | 57 | 131 | 88 | 42 | 93 |
| 10 | 69 | 56 | 70 | 129 | 23 | 57 |
| 11 | 27 | 63 | 59 | 100 | 17 | 81 |
| 12 | 40 | 40 | 23 | 107 | 22 | 52 |
| 13 | 56 | 52 | 25 | 85 | 43 | 75 |
| 14 | 40 | 95 | 33 | 65 | 20 | 87 |
| 15 | 85 | 89 | 71 | 100 | 11 | 78 |
| 16 | 41 | 63 | 16 | 60 | 0 | 79 |
| 17 | 52 | 56 | 30 | 69 | 22 | 52 |
| 18 | 55 | 63 | 33 | 112 | 33 | 56 |
| 19 | 36 | 71 | 40 | 69 | 33 | 52 |

During the study, Patient 3 reported that during her use of the N-Acetyl Methyl GABA composition, her menstrual cycle occurred, and she did not experience cramping. She further advised she usually cramps heavily during her cycle and that this is the first time she did not experience bad cramps. Patient 3 also reported less night sweats from perimenopause.

During the study, Patient 18 reported that she is currently experiencing Menopause symptoms and that her symptoms seemed to be reduced. She also reported a reduction in mood swings and in irritability.

During the study, Patient 15 reported taking Lexapro® (escitalopram) for anxiety. She further reported that she felt like she could stop taking Lexapro with the N-Acetyl Methyl GABA composition, and that her pre-menstrual cycle (PMS) symptoms were reduced when taking the N-Acetyl Methyl GABA composition (GabaSorb®).

Figure 4:
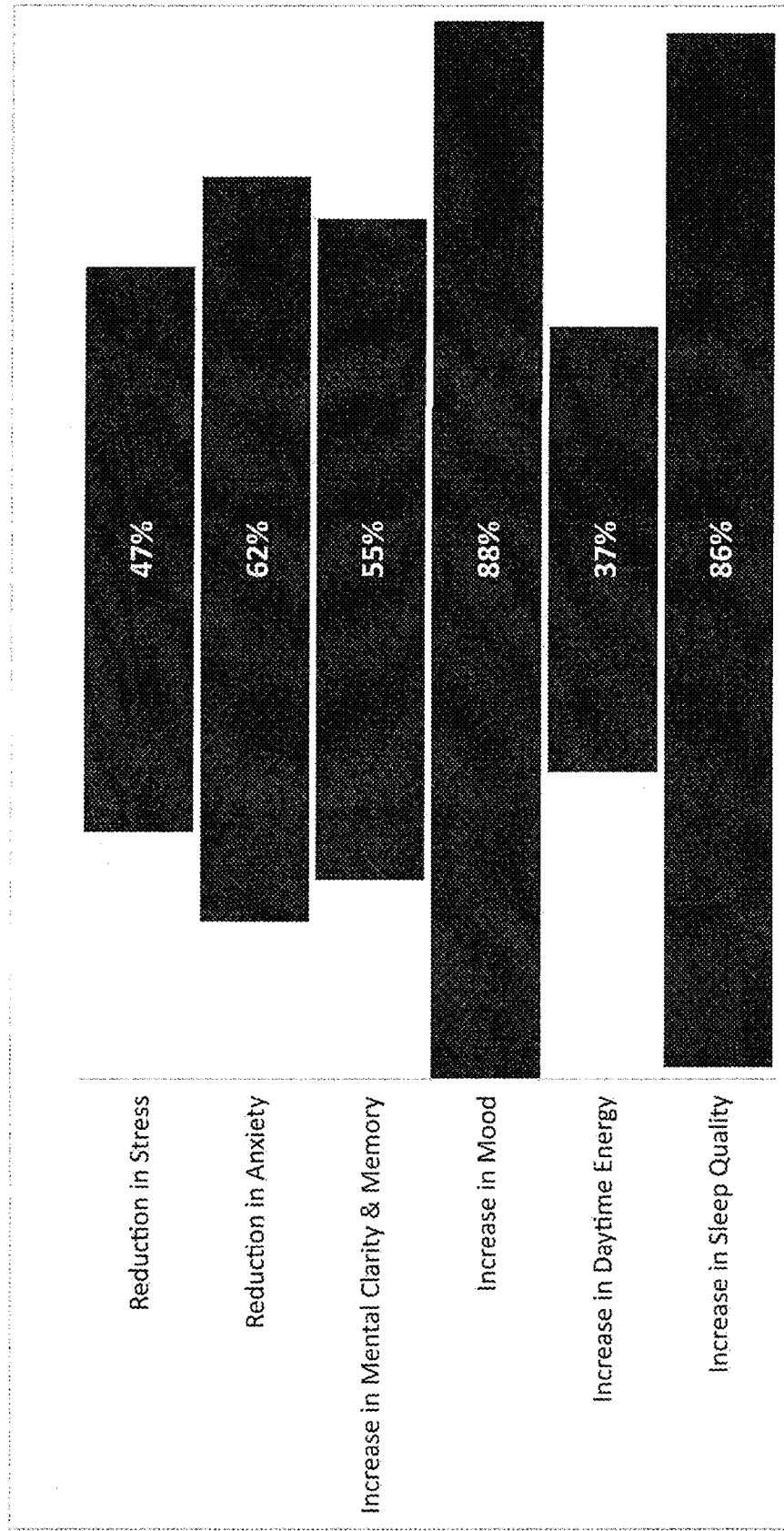
FIG. 4 is a bar graph representing a summary of improvements in 19 subjects' stress, anxiety, mental clarity and memory, mood, daytime energy, and sleep quality after administration of an N-Acetyl Methyl GABA composition of this invention.

Table 13 and FIG. 4 show a summary of patient outcomes in this study with administration of an N-Acetyl Methyl GABA composition of this invention.

TABLE 13

Summary of Daytime Study, 19 Human Patient Outcomes

| Type of Change | Quality/Symptom | % Change |
|---|---|---|
| Reduction in Symptoms | Stress | 47 |
| Reduction in Symptoms | Anxiety | 62 |

TABLE 13-continued

Summary of Daytime Study, 19 Human Patient Outcomes

| Type of Change | Quality/Symptom | % Change |
|---|---|---|
| Increase in Quality | Mental Clarity and Memory | 55 |
| Increase in Quality | Mood | 88 |
| Increase in Quality | Daytime Energy | 37 |
| Increase in Quality | Sleep Quality | 86 |

Discussion

Figure 3:
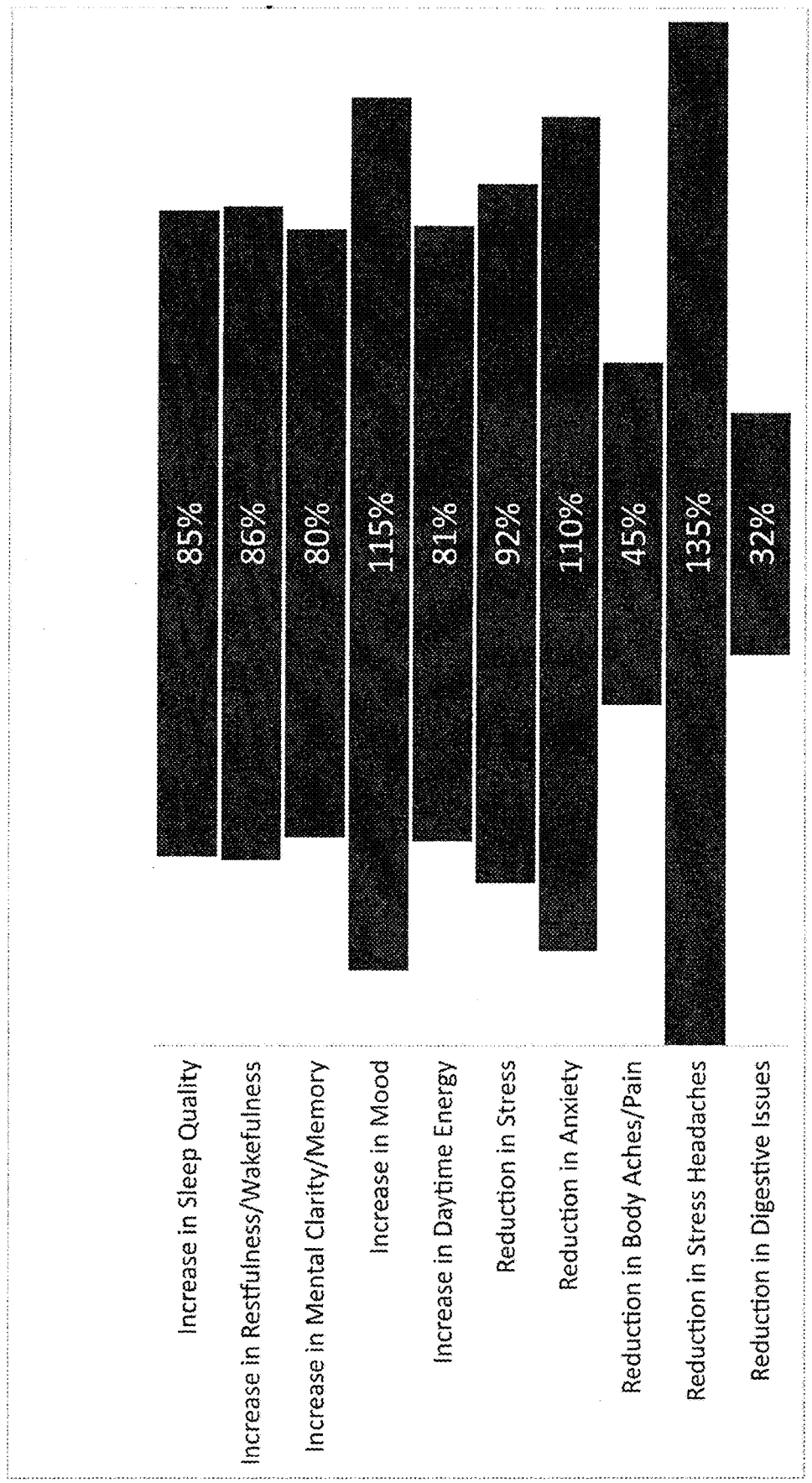
FIG. 3 is a bar graph representing a summary of improvements in 47 subjects' sleep quality, restfulness/wakefulness, mental clarity and memory, mood, daytime energy, stress, anxiety, body aches/pains, stress headaches, and digestive issues after administration of an N-Acetyl Methyl GABA composition of this invention for a nighttime sleep period.

FIG. 3 summarizes improvements experienced by 47 subjects after 14 days' nighttime administration of an N-Acetyl Methyl GABA composition of this invention, including a daily dose of 300 mg N-Acetyl Methyl GABA and 5 mg melatonin. As shown in FIG. 3, overall the composition provided a 92% reduction in stress and 110% reduction in anxiety in the subjects. Subjects further reported an 85% improvement in sleep quality, 86% improvement in restfulness/wakefulness, an 80% improvement in mental clarity and memory, a 115% improvement in mood, and an 81% improvement in daytime energy, as well as a reduction in body aches and pains by 45%, 135% reduction in stress headaches, and 32% reduction in digestive issues, all after administration of an N-Acetyl Methyl GABA composition for 14 consecutive nighttime sleep periods.

FIG. 4 summarizes further studies showing improvements in 19 subjects' stress, anxiety, mental clarity and memory, mood, daytime energy, and sleep quality after administration of a 300 mg daily dose of an N-Acetyl Methyl GABA composition, at a time of the subject's choosing and without melatonin, for 14 consecutive days. As shown in FIG. 4, overall the composition provided a 47% reduction in stress and 62% reduction in anxiety, as well as a 55% improvement in mental clarity and memory, 88% improvement in mood, 37% improvement in daytime energy, and 86% improvement in sleep quality.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All method steps described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification the present invention has been described in relation to certain embodiments thereof, and many details have been put forth for the purposes of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

The invention claimed is:

1. A method of reducing anxiety and/or reducing stress in a subject comprising the steps of:
   a. providing a composition comprising N-Acetyl Methyl GABA; and
   b. administering the composition to the subject in an amount effective to increase the amount of N-Acetyl Methyl GABA in the subject's bloodstream and brain tissue to reduce anxiety and/or stress in the subject.

2. The method of claim 1, wherein said administering step (ii) occurs less than 1 hour before a sleep period.

3. The method of claim 1, wherein said effective amount is a daily dose of 200-600 mg N-Acetyl Methyl GABA.

4. The method of claim 3, wherein said dose is about 300 mg N-Acetyl Methyl GABA.

5. The method of claim 1, wherein mental clarity and memory, mood, daytime energy, and/or sleep quality are improved in the subject.

6. The method of claim 1, wherein body aches and pains, inflammation, irritability, stress headaches, menstrual cramps, mood swings, menopausal night sweats, and/or digestive problems are decreased in the subject.

7. The method of claim 1, wherein said administration occurs for at least 3 consecutive days.

8. The method of claim 1, said composition comprising about 1-10 mg melatonin.

9. The method of claim 1, said composition comprising about 0.05% to about 0.1% w/w of melatonin.

10. The method of claim 7, wherein said administration occurs for 14 consecutive days.

11. The method of claim 1, wherein in said administering step, said composition is administered orally.

12. The method of claim 1, said composition comprising:
    about 70% w/w deionized water,
    about 14.5% w/w glycerine,
    about 7.1% w/w soy lecithin liquid,
    about 3.8% w/w N-Acetyl Methyl GABA,
    about 1.3% w/w orange flavor liquid,
    about 1.0% w/w sodium lauroyl lactylate,
    about 0.38% w/w stevia extract 90%,
    about 0.35% w/w bitter mask powder,
    about 0.35% w/w Luo Han Guo 50%,
    about 0.31% w/w guar gum,
    about 0.28% w/w potassium sorbate,
    about 0.25% w/w curcumin 95%,
    about 0.22% w/w Vitamin E oil,
    about 0.125% w/w peppermint oil,
    about 0.125% w/w cinnamon oil, and
    about 0.06% w/w melatonin.

13. The method of claim 12, wherein said N-Acetyl Methyl GABA is about 300 mg.

14. The method of claim 1, said composition comprising:
    about 62.1% w/w deionized water,
       about 14.8% w/w glycerine,
       about 5.8% w/w MCT oil 60/40,
       about 5.0% w/w soy lecithin liquid,
       about 3.8% w/w N-Acetyl Methyl GABA,
       about 2.3% w/w orange flavor liquid,
       about 1.9% w/w xylitol,
       about 0.7% w/w sodium lauroyl lactylate,
       about 0.6% w/w stevia extract 90%,
       about 0.6% w/w bitter mask powder,
       about 0.6% w/w Luo Han Guo 50%,
       about 0.4% w/w peppermint oil,
       about 0.3% w/w guar gum,
    about 0.3% w/w cinnamon oil,
    about 0.25% w/w potassium sorbate,
    about 0.23% w/w Vitamin E oil, and
    about 0.06% w/w melatonin.

15. The method of claim 14, wherein said composition is in liquid form and said N-Acetyl Methyl GABA is about 300 mg.

16. The method of claim 1, said composition comprising:
    about 62.4% w/w deionized water,
    about 14.8% w/w glycerine,
    about 5.8% w/w MCT oil 60/40,
    about 5.0% w/w soy lecithin liquid,
    about 3.8% w/w N-Acetyl Methyl GABA,
    about 2.3% w/w orange flavor liquid,
    about 1.9% w/w xylitol,
    about 0.7% w/w sodium lauroyl lactylate,
    about 0.6% w/w stevia extract 90%,
    about 0.6% w/w bitter mask powder,
    about 0.6% w/w Luo Han Guo 50%,
    about 0.4% w/w peppermint oil,
    about 0.3% w/w guar gum,
    about 0.3% w/w cinnamon oil,
    about 0.25% w/w potassium sorbate, and
    about 0.23% w/w Vitamin E oil.

17. The method of claim 16, wherein said composition is in liquid form and said N-Acetyl Methyl GABA is about 300 mg.

18. The method of claim 1, wherein said effective amount is a daily dose of about 10 mg to about 1000 mg N-Acetyl Methyl GABA.

* * * * *